United States Patent [19]
Roseman et al.

[11] Patent Number: 5,985,644
[45] Date of Patent: *Nov. 16, 1999

[54] BACTERIAL CATABOLISM OF CHITIN

[75] Inventors: Saul Roseman, Baltimore, Md.; Bonnie Bassler, Princeton, N.J.; Nemat O. Keyhani, Balitmore, Md.; Edith Chitlaru, Rehovot, Israel; Charles Yu, Lutherville, Md.

[73] Assignee: The Johns Hopkins University, Baltimore, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/600,452

[22] Filed: Feb. 13, 1996

Related U.S. Application Data

[63] Continuation-in-part of application No. 08/386,727, Feb. 13, 1995.

[51] Int. Cl.⁶ .............................. C12N 1/20; C12N 9/24; C12N 1/00; C07H 21/04
[52] U.S. Cl. ...................... 435/252.3; 435/200; 435/209; 435/320.1; 435/909; 536/23.2; 536/23.7
[58] Field of Search ..................................... 435/200, 209, 435/252.3, 320.1, 69.1, 909; 536/23.2, 23.7

[56] References Cited

PUBLICATIONS

C. Yu, A. Lee, B. Bassler, and S. Roseman; (Chitin Utilization by Marine Bacteria); Oct. 18, 1990; The Journal of Biological Chemistry; vol. 266, No. 36, Issue of Dec. 25, pp. 24260–24267, 1991.
B. Bassler, P. Gibbons, C. Yu, and S. Roseman; (Chitin Utilization by Marine Bacteria); Oct. 18, 1990; The Journal of Biological Chemistry; vol. 266, No. 36, Issue of Dec. 25, pp. 24268–24275, 1991.
B. Bassler, C. Yu, Y.C. Lee, and S. Roseman; (Chitin Utilization by Marine Bacteria); Oct. 18, 1990; The Journal of Biological Chemistry; vol. 266, No. 36, Issue of Dec. 25, pp. 24276–24286, 1991.
C. Yu, B. Bassler, and S. Roseman: (Chemotaxis of the Marine Bacterium *Vibrio Furnissii* to Sugars); The Journal of Biological Chemistry; vol. 268, No. 13, Issue May 5, pp. 9405–9409, 1993.
C. Yu, A. Lee, And S. Roseman; The Sugar–Specific Adhesion/Deadhesion Apparatus of the Marine Bacterium *Vibrio Furnssii*; Biochemical and Biophysical Research Communications; vol. 149, No. 1, Nov. 30, 1987.
B. Bassler, P. Gibbons, and S. Roseman; (Chemotaxis to Chitin Oligosaccharides by *Vibrio Furnissii;* Biochemical and Biophysical Research Communications; vol. 161, No. 3, Jun. 30, 1989.
P. Lerouge; (Symbiotic Host Specificity between leguminous plants and rhizobia is determined by substituted and acylated glucosamine oligosaccharide signals; Oxford University Press, Mini Review; pp. 127–134.
Bassler, et al., *Chitin Utilization by Marine Bacteria,* The Journal of Biological Chemistry, 266(36):24268, Dec. 1991.
Don R. Durham, *The Unique Stability of Vibrio proteolyticus Neutral Protease under Alkaline Conditions Affords a Selective Step for Purification and Use in Amino Acid–Coupling Reactions,* Applied and Environmental Microbiology, 56(8):2277, Aug. 1990.
Jannatipour, et al., *Translocation of Vibrio harveyi, N, N'–Diacetylchitobiase to the Outer Membrane of Escherichia coli,* Journal of Bacteriology, 169(8):3785, Aug. 1987.
Soto–Gil and Zyskind, *N,N'–Diacetylchitobiase of Vibrio harveyi,* The Journal of Biological Chemistry, 264(25):14778, Sep. 1989.
Takahashi, et al., *Purification and Some Characteristics of β–N–Acetylglucosaminidase Produced by Vibrio sp.,* Journal of Fermentation and Bioengineering, 76(5):356, 1993.
Tsujibo, et al., *Molecular Cloning of the Gene Which Encodes β–N–Acetylglucosaminidase from a Marine Bacterium,* Alteromonas sp. Strain 0–7, Applied and Environmental Microbiology, 61(2):804, Feb. 1995.
Yamano, et al., *Production of N–Acetylglucosamine Deacetylase by Vibrio cholerai Non–01,* Biosci. Biotech Biochem., 58(1):193, 1994.
Zhu, et al., *Thermostable, Salt Tolerant, Wide pH Range Novel Chitobiase from Vibrio parahemolyticus: Isolation, Characterization, Molecular, Cloning, and Expression,* J. Biochem, 112:163, 1992.

*Primary Examiner*—Robert A. Wax
*Assistant Examiner*—Tekchand Saidha
*Attorney, Agent, or Firm*—Linda M. Buckley; Robert L. Buchanan; Dike, Bronstein, Roberts & Cushman, LLP

[57] ABSTRACT

Three genes involved in the catabolism of chitin in *Vibrio furnissii*: endI encodes periplasmic chitodextrinase, exoI encodes periplasmic β-N-acetylglucosaminidase, and exoII encodes aryl β-N-acetylglucosaminidase are provided. The complete nucleotide sequence for each of the three genes and the complete amino acid for the corresponding enzymes are demonstrated along with host cells capable of expressing the recombinant enzymes. The present invention also describes four specific strains of *V. furnissii* having deletions in genes involved in the catabolic pathway of chitin and a process for the production of chitin oligosaccharides.

6 Claims, 7 Drawing Sheets

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 6180 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
TATTCCCGTA AAACAATAAC TTAAGGAAAT AAAAATGCGC TTACATCGAG CTAAAGTGTC      60

GAAGAGTGTC TTTACGCTCA GCACTTTGAC GGCTTCGTGC CTCATGGCGT TCAACAGCTA     120
```

```
TGCAGCGGTG GATTGTTCTG CTCTGGCGGA GTGGCAATCT GACACAATTT ATACTGGCGG      180

CGATCAGGTT CAATACAACG GGTCTGCGTA TCAGGCCAAT TATTGGACGC AGAATAACGA      240

TCCGGAGCAG TTCTCCGGTG ATTACGCGCA GTGGAAACTG CTAGATGCTT GTACGACCGA      300

CGGTGGCGAT GACAATCAGG CTCCCAATGC GACATTGACC TCTCCGTCGG CGTCGGATGT      360

GTTGACAACC GGAGATGTGG TGACGCTGGC GGCCAGCGCG TCAGACAACG ACGGGACGAT      420

CGCACGTGTC GATTTTCTGG TTGATGGTGT GGTGGTTGCC CAAGCGAGCA GTGCACCCTA      480

CAGCGCCACA TGGACGGCGG TCGCCGGAAC ACACCAAATC AGCGCCATTG CTTATGATGA      540

CAAGGCACTT GCCAGCACGG CGAGTCAAGT CTCTGTTTCG GTGACAGACA GCACGCAACC      600

GGGCAACGAA GCGCCAACGG TAGACATCAC GTTGTCTGCC AGCCAAGTGG ATGTGGGGA      660

CGTGGTGACG CTCACGGCCA ATGCTGCAGA CGCTGATGGC AGTGTCGACA AGTTGATTT      720

TTACGTGGCC GGCTCTCTTG TGGGAACAGT CGCTTCTACA CCTTACACTT  TGGATTACAC     780

CACCACCCGT TCGGGCGCT GGCTGTGTTT GCGCGCGCGA CTGATAACGT CGGCGCGACA      840

ACGGATTCGA CCGCGGCGAC GCCTGACGGT GGCTGCTGGT CCGTGGTCAG TACCTGTCGT      900

CCTGATGGTT TGTATCAAAC CGAAGGGTCA GTGTGCCGTA TTGTACGGTG TACGTGAAGA      960

TGGCCGCGAG AAAATGGGTG CCGATCACCC CCGTCGCGTC ATTGGGTATT TCACCAGTTG     1020

GCGAGCGGGA GACGATGATC AGACCGCTTA CTTGGTTAAA GACATTCCTT GGGAACAGCT     1080

TACGCACATC AACTACGCGT TTGTCAGCAT TGGTTCTGAT GGCAAAGTCA ATGTCGGTGA     1140

TGTCAACGAT GCCAATAACG CGGCGGTTGG AAAAGAGTGG GATGGCGTTG AAATTGACCC     1200

AACGCTGGGC TTTAAAGGCC ATTTCGGCGC ACTGGCAACC TACAAGCAAA ATATGGTGT      1260

GAAAACGCTG ATCTCGATTG GCGGCTGGGC CGAAACGGGC GGGCATTTTG ACAATGATGG     1320

CAATCGTGTT GCGGATGGCG GTTTCTATAC CATGACCACC AACGCAGACG GTTCGATTAA     1380

TCAACAAGGC ATTGAAACCT TGCTGATTC CGCAGTTGAA ATGATGCGAA ATACCGTTT      1440

CGATGGATTG GACATTGACC TACGAATATC AACATCGAT GGCGGGACGG GCAATCCTGA      1500

CGACACCGCA TTCTCTGAAT CACGCCGTGC TTACCTGATG AATTCTTATC ACGAACTGAT     1560

GCGTGTGCTG CGTGAAAAAC TGGATGTAGC GAGCGCTCAA GATGGTGTGC ATTACATGCT     1620

GACCATTGCC GCGCCATCAT CGGCTTATCT GCTACGTGGT ATGGAAACCA TGGCGGTGAC     1680

TCAGTACCTT GATTACGTGA ACATCATGTC CTACGACTTA CATGGTGCGT GGAACGATCA     1740

TGTCGGTCAC AACGCAGCAC TGTACGACAC CGGGAAGGAT TCTGAACTGG CACAATGGAA     1800

TGTGTACGGC ACGGCGCAAT ATGGCGGTAT TGGTTACCTC AACACCGATT GGGCATTCCA     1860

CTATTTCCGC GGTTCAATGC CAGCGGGTCG CATCAACATT GGCGTGCCTT ACTACACCCG     1920

CGGTTGGCAG GGCGTCACTG GTGGTGATAA TGGCCTTTGG GGCGCGCGGC TTGCCAAATC     1980

AAAGCGAGTG TCCAACCGGT ACGGCGAGGG CGAGAAAAAC AACTGCGGTT ACGGCGCGAC     2040

GGGCCTAGAT AACATGTGGC ACGATGTCAA CGCCGCTGGT GATGAGATGG CGCAGGTTC      2100

TAACCCAATG TGGCATGCTA AAAACTTGGA GCACGGCATT TGGGGTTCCT ATTTAGCGGT     2160

CTATGGTTTG GATCCAACCA CCGCACCGTT GGTTGGCACG TATGCCCGTA ATTACGACAG     2220

TGTGGCGATT GCGCCATGGC TTTGGAACGC AGAGAAGAAA GTGTTCCTGT CGACGGAAGA     2280

CAAGCAATCC ATTGATGTAA AAGCAGATTA CGTGATCGAT AAAGAGATCG GCGGCATCAT     2340

GTTCTGGGAA CTCGCGGGAG ACTACAACTG CTACGTGCTC GATGCCAACG GCCAACGCAC     2400

CAGCATTGAT AGCACGGAAC AGGCGTGTGA AAGCGGTCAA GGTGAATACC ACATGGGGAA     2460

CACCATGACC AAAGCCATTT ACGACAAGTT CAAAGCGGCG ACGCCATATG GCAACACCGT     2520
```

```
GGCGACGGGC GCGGTTCCGT CTGAAACCGT CGATATCGCT GTGTCGATTG GCGGTTTTAA    2580

AGTGGGCGAC CAGAACTACC CAATCAATCC GAAAGTCACC TTTACCAACA ACACGGGCGT    2640

TGATATTCCC GGTGGCACGG CATTCCAGTT CGACATTCCG GTTTCTGCGC CAGATAATGC    2700

CAAAGACCAA TCGGGTGGTG GTTTGAGCGT GATTGCCTCT GGTCATACGC GTGCAGATAA    2760

CATCGGCGGT TTGGATGGCA CAATGCACCG CGTCGCGTTC TCGCTGCCTG CGTGGAAAAC    2820

GCTACCAGCG GGCGACACGT ACGAGTTGGA CATGGTGTAC TACTTGCCGA TTTCAGGGCC    2880

AGCAAACTAC AGCGTGAACA TTAACGGCGT GGATTATGCC TTTAAGTTTG AACAACCTGA    2940

TTTGCCGCTC GCGGATCTCT CGTCAGGAAA TGGGGGGGGC ACCGGCGGTG GCGACACTGG    3000

CGGCGGAACG ACTGAGCCGG GTGATGTTGT GGAATGGGTA CCCGGTTCGA CGCAAGTGAG    3060

CGATGGCACG ACGGTGACCT ACAACGGCAA GTGCTTTGTG GCGCAAAACA GCCCAGGCGT    3120

GTGGGAAAGC CCAACCCAGA CCAATTGGTT CTGGGAGGAA GTGACCTGCC CGTAAAGGGA    3180

AGCCACTGTG AAAAAACCGT CCTTCGGGGC GGTTTTTTGT GTGACGGATA AGCGATACAA    3240

CGCGCTCAGA ACAATAGTGT CGAATGCGAA GCCTTAACTC GCATGATACT TAACTCGCTG    3300

ATAGGAGTGA AGGCTTCGCG TCGGCGTGAC TCATGCATGG CTCACGAAGG AGGCGTGAAT    3360

TGATAGCAAA CCGGCACCAC CACAATCCCT TTTTCAGAAA TTTGGAAGCG TTTGGCATCC    3420

TCAATTCGGT TTAAGCCAAT TTGCGTGTGC GGCGGAATTT TAACGTGCTT GTCGATGATG    3480

CAGTTGACCA ACTGACAACC ATCGCCCACT TCCACATCAT CAAACAAAAT GCTGTCGACA    3540

ATGGTGGCGC CGTCGTTGAT GCGCACACCG GAAGAGACAA TCGAGTGCTG CACCGAGCCG    3600

CCCGAGTTGA TCACGCCGTT GGAAATGATG GAGTTGATAA AGATTCCTTC ATTCCCCGTG    3660

GCCGATGACA CCGTACGTGC TGGCGGAAGC TGTGGTTCGT ACGTACGAAT CGCCCAGTTT    3720

TTTTGGTACA AATTCATGGG CGGAACCGGC TCAAGTAAAT CCATATTGGC TTCATAAAAT    3780

GAGTCAATCG TGCCTACATC GCGCCAGTAG CAATCTTTCG CGACGCGCCC TTTGTCATTG    3840

CCAAACTGAT ATGCGTATAC GCTTTGGGTT GGGATCAGTT TTGGAATGAT GTCTTTGCCA    3900

AAGTCATGAC TTGAACCACT GTTTTCTGAG TCTTCATTCA GCGCTTGTTG GAGCGTTTCC    3960

ATATTAAAAA TATAGATGCC CATCGAGGCC AAACTGCGAT CAGGTTGTGA AGGCATCGCG    4020

GGGGATCGC TTGGCTTCTC AACAAATGAG GTAATACGGT GTTCATCATC AATGGCCATC    4080

ACGCCAAACG CTTTGGCTTC TTCGCGTGGC ACATCCATGC AAGCGATTGT CAGCGTGGCG    4140

CCTTTCTCAA TGTGCTCTTC CAGCATCGCG CATAATCCAT GCGGTAAATA TGATCGCCGG    4200

ACAGCACAAC GACGTGCTTG GCATCGCTGC GTGACAGTAG CCACATGTTG TGAAACAGCG    4260

CATCGGCTGT TCCTTCGTAC CATTTGGCCA CCTTTGCGCA TTTGTGGGGG GACCACAGTA    4320

ATGAACTCGC CCAATTCGGG GTTAAAAATG GACCAGCCAT CACGCAGGTG TTTCTGCAAT    4380

GAATGCGATT TGTATTGTGT CAGCACCAAA ATGCGGCGTA AGCCTGAGTG CAGACAGTTC    4440

GTGAGGGTAA AATCGACTGA TGCGATATTT GCCGCCAAAT GGTACGGCGG GTTTTGCGCG    4500

ATCATCGGTG AGGGGGAAA GTCGTGAGCC CATACCGCCG GCCAACACGA CTGCTAAGGT    4560

ATCTTGCATC TTTTACTCCC TAATCATGTG CAATTCATAA CCACTTTAGA GAGTAGTACA    4620

AGTTTCACGC CACAATTGGA ATGACCGTCA AATATGGGAT GTGCGTAGTT TAGTTGTTAC    4680

TAATGCACTA AAACAAGGCA TCTTGTGCGT TAAAATTGCA CCGTGTTGGT GCTGTGAAAA    4740

TAGAGGATGA TTAAGCGAAG TGAACCATTT CTGCGCTGGT GAGCACGGAG ACGACATTTC    4800

GGCCTGACTC TTTGGATTCG TACAAGGCCA TGGTCGGCAC GTTGATACAC TTCTTCAGGC    4860

ACTTCAGTGA TATCCGTCAG GCCGCCGCTG ACGGATAAAT CCCCTTGATG GAGATCGAAC    4920
```

-continued

```
ACCGCCACGC GAAGCCGATT GAGGACGGTT TCCGCTTCAT CGATTGGTGT GTGAGGCAAA    4980

ATGATGGCAA ATTCTTCGCC ACCAATTCGT GCAAGAAAGT CTGATTCGCG CAGTTCATTG    5040

CGCAAACATT GGGCAACGGC ACGAATGGTT TTATCGCCGC GCGCGTGGCC ATATTTGTCA    5100

TTGATGCGCT TGAAGTGATC AATATCGAGA ATCGCCAAGC ACGATTGCTC GTGTGCCGGA    5160

TAGCGTTTGA CACGCATGCA TTCCGAGCGG AATTCTTGAT CAAATTTACG TCGGTTCCAG    5220

ATGTTGGATA ATCCATCTTT TTCACTTTGG TCACGCAATT GGTCTTCCAG CAACTTGCGT    5280

TCAGTGATGT CAACAAACGA CGCCACGTAG AACTGAATGA TGTCGTCATC ATCCAAAATG    5340

GTCTGAATAC GTAAGATCTC CGTGAGCATC GAGCCATCTT TACGTTGGTT GATCACTTCG    5400

CCTTCCCAGA AGCCGTCATT CTGCAGCGCC TGCCACATCT CGACATAAAA TTCTGACGTG    5460

TGTTTTCCAG AGGCAAACAT CGATGGTTGT TGCCCGCTCA CTTCTTCAAA GCTGTAGCCA    5520

CTCAGGCGGG TAAACTCATT GTTGACCTTG ATGATGCGAT TATTGCGGTC GGTGATGATC    5580

ACCGCCGACA TGCCATTCAT CGCCGCGCGC GCCAATTTAC TCTCAATGCT GTTTTTCTGA    5640

TGGTTGTTGT TCCACAGCAC GAAGATCGAG GCAATCAGGC AAATCAGCGC AAACAGGGCA    5700

ACCATTTGTA GGGTTAACGT GTTTTTGCTG TTGTGCATCA AGGCATGGAT TTCGCTATTC    5760

TCAACACGCT CCAATAACAC CACCGAGGGC ACGTTGACCA ACGATGCGTT TGGCGAAATC    5820

TTCACAAAAC TGAACCATTG ACCGTTTTCG GAAATGGTGC CTTGTTCGTC AGAAAGAATG    5880

GTATGCCAAA GCTGCGGGAA ACGCTGCGCC AAATTAGTGA GCGCGGTACG ATCGTTTGAT    5940

TCCTCCAGCC GCTGACTCAT CAACACATCC CCGTTGAGGT TCAGAATATC GGGCAGCATG    6000

GCTCGGCGAT TGCTGCCAGC AATTTGCTGA TAAATGTAGT TCAGATTGAT GTTTGCGACG    6060

AAATAGCCTT TGCGCTCGCC ATCAAGTTCG ATTGGGGAGA CAAAATAGAG CGATGGTTTG    6120

GTGGGCGTCA TGTCGTCGCC AGTCGATTGC ACACCAAACA CGCCGATTTG CCCCGCAGAC    6180
```

(2) INFORMATION FOR SEQ ID NO:2:

(i) SEQUENCE CHARACTERISTICS:
        (A) LENGTH: 1046 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Arg Leu His Arg Ala Lys Val Ser Lys Ser Val Phe Thr Leu Ser
  1               5                  10                  15

Thr Leu Thr Ala Ser Cys Leu Met Ala Phe Asn Ser Tyr Ala Ala Val
             20                  25                  30

Asp Cys Ser Ala Leu Ala Glu Trp Gln Ser Asp Thr Ile Tyr Thr Gly
         35                  40                  45

Gly Asp Gln Val Gln Tyr Asn Gly Ser Ala Tyr Gln Ala Asn Tyr Trp
     50                  55                  60

Thr Gln Asn Asn Asp Pro Glu Gln Phe Ser Gly Asp Tyr Ala Gln Trp
 65                  70                  75                  80

Lys Leu Leu Asp Ala Cys Thr Thr Asp Gly Gly Asp Asp Asn Gln Ala
                 85                  90                  95

Pro Asn Ala Thr Leu Thr Ser Pro Ser Ala Ser Asp Val Leu Thr Thr
            100                 105                 110

Gly Asp Val Val Thr Leu Ala Ala Ser Ala Ser Asp Asn Asp Gly Thr
        115                 120                 125
```

-continued

```
Ile Ala Arg Val Asp Phe Leu Val Asp Gly Val Val Ala Gln Ala
    130                 135                 140

Ser Ser Ala Pro Tyr Ser Ala Thr Trp Thr Ala Val Ala Gly Thr His
145                 150                 155                 160

Gln Ile Ser Ala Ile Ala Tyr Asp Asp Lys Ala Leu Ala Ser Thr Ala
                    165                 170                 175

Ser Gln Val Ser Val Ser Val Thr Asp Ser Thr Gln Pro Gly Asn Glu
                180                 185                 190

Ala Pro Thr Val Asp Ile Thr Leu Ser Ala Ser Gln Val Asp Val Gly
            195                 200                 205

Asp Val Val Thr Leu Thr Ala Asn Ala Ala Asp Ala Asp Gly Ser Val
        210                 215                 220

Asp Lys Val Asp Phe Tyr Val Ala Gly Ser Leu Val Gly Thr Val Ala
225                 230                 235                 240

Ser Thr Pro Tyr Thr Leu Asp Tyr Thr Thr Arg Ser Gly Arg Trp
                    245                 250                 255

Leu Cys Leu Arg Ala Arg Leu Ile Thr Ser Ala Arg Gln Arg Ile Arg
                260                 265                 270

Pro Arg Arg Leu Thr Val Ala Gly Pro Trp Ser Val Pro Val
            275                 280                 285

Val Leu Met Val Cys Ile Lys Pro Lys Gly Gln Cys Ala Val Leu Tyr
        290                 295                 300

Gly Val Arg Glu Asp Gly Arg Glu Lys Met Gly Ala Asp His Pro Arg
305                 310                 315                 320

Arg Val Ile Gly Tyr Phe Thr Ser Trp Arg Ala Gly Asp Asp Gln
                    325                 330                 335

Thr Ala Tyr Leu Val Lys Asp Ile Pro Trp Glu Gln Leu Thr His Ile
                340                 345                 350

Asn Tyr Ala Phe Val Ser Ile Gly Ser Asp Gly Lys Val Asn Val Gly
            355                 360                 365

Asp Val Asn Asp Ala Asn Asn Ala Ala Val Gly Lys Glu Trp Asp Gly
        370                 375                 380

Val Glu Ile Asp Pro Thr Leu Gly Phe Lys Gly His Phe Gly Ala Leu
385                 390                 395                 400

Ala Thr Tyr Lys Gln Lys Tyr Gly Val Lys Thr Leu Ile Ser Ile Gly
                    405                 410                 415

Gly Trp Ala Glu Thr Gly Gly His Phe Asp Asn Asp Gly Asn Arg Val
                420                 425                 430

Ala Asp Gly Gly Phe Tyr Thr Met Thr Thr Asn Ala Asp Gly Ser Ile
            435                 440                 445

Asn Gln Gln Gly Ile Glu Thr Phe Ala Asp Ser Ala Val Glu Met Met
        450                 455                 460

Arg Lys Tyr Arg Phe Asp Gly Leu Asp Ile Asp Leu Arg Ile Ser Asn
465                 470                 475                 480

Ile Asp Gly Gly Thr Gly Asn Pro Asp Asp Thr Ala Phe Ser Glu Ser
                    485                 490                 495

Arg Arg Ala Tyr Leu Met Asn Ser Tyr His Glu Leu Met Arg Val Leu
                500                 505                 510

Arg Glu Lys Leu Asp Val Ala Ser Ala Gln Asp Gly Val His Tyr Met
            515                 520                 525

Leu Thr Ile Ala Ala Pro Ser Ser Ala Tyr Leu Leu Arg Gly Met Glu
        530                 535                 540

Thr Met Ala Val Thr Gln Tyr Leu Asp Tyr Val Asn Ile Met Ser Tyr
545                 550                 555                 560
```

-continued

```
Asp Leu His Gly Ala Trp Asn Asp His Val Gly His Asn Ala Ala Leu
            565                 570                 575

Tyr Asp Thr Gly Lys Asp Ser Glu Leu Ala Gln Trp Asn Val Tyr Gly
            580                 585                 590

Thr Ala Gln Tyr Gly Gly Ile Gly Tyr Leu Asn Thr Asp Trp Ala Phe
            595                 600                 605

His Tyr Phe Arg Gly Ser Met Pro Ala Gly Arg Ile Asn Ile Gly Val
            610                 615                 620

Pro Tyr Tyr Thr Arg Gly Trp Gln Gly Val Thr Gly Asp Asn Gly
625                 630                 635                 640

Leu Trp Gly Ala Arg Leu Ala Lys Ser Lys Arg Val Ser Asn Arg Tyr
            645                 650                 655

Gly Glu Gly Glu Lys Asn Asn Cys Gly Tyr Gly Ala Thr Gly Leu Asp
            660                 665                 670

Asn Met Trp His Asp Val Asn Ala Ala Gly Asp Glu Met Gly Ala Gly
            675                 680                 685

Ser Asn Pro Met Trp His Ala Lys Asn Leu Glu His Gly Ile Trp Gly
            690                 695                 700

Ser Tyr Leu Ala Val Tyr Gly Leu Asp Pro Thr Thr Ala Pro Leu Val
705                 710                 715                 720

Gly Thr Tyr Ala Arg Asn Tyr Asp Ser Val Ala Ile Ala Pro Trp Leu
            725                 730                 735

Trp Asn Ala Glu Lys Lys Val Phe Leu Ser Thr Glu Asp Lys Gln Ser
            740                 745                 750

Ile Asp Val Lys Ala Asp Tyr Val Ile Asp Lys Glu Ile Gly Gly Ile
            755                 760                 765

Met Phe Trp Glu Leu Ala Gly Asp Tyr Asn Cys Tyr Val Leu Asp Ala
            770                 775                 780

Asn Gly Gln Arg Thr Ser Ile Asp Ser Thr Glu Gln Ala Cys Glu Ser
785                 790                 795                 800

Gly Gln Gly Glu Tyr His Met Gly Asn Thr Met Thr Lys Ala Ile Tyr
            805                 810                 815

Asp Lys Phe Lys Ala Ala Thr Pro Tyr Gly Asn Thr Val Ala Thr Gly
            820                 825                 830

Ala Val Pro Ser Glu Thr Val Asp Ile Ala Val Ser Ile Gly Gly Phe
            835                 840                 845

Lys Val Gly Asp Gln Asn Tyr Pro Ile Asn Pro Lys Val Thr Phe Thr
850                 855                 860

Asn Asn Thr Gly Val Asp Ile Pro Gly Gly Thr Ala Phe Gln Phe Asp
865                 870                 875                 880

Ile Pro Val Ser Ala Pro Asp Asn Ala Lys Asp Gln Ser Gly Gly Gly
            885                 890                 895

Leu Ser Val Ile Ala Ser Gly His Thr Arg Ala Asp Asn Ile Gly Gly
            900                 905                 910

Leu Asp Gly Thr Met His Arg Val Ala Phe Ser Leu Pro Ala Trp Lys
            915                 920                 925

Thr Leu Pro Ala Gly Asp Thr Tyr Glu Leu Asp Met Val Tyr Tyr Leu
            930                 935                 940

Pro Ile Ser Gly Pro Ala Asn Tyr Ser Val Asn Ile Asn Gly Val Asp
945                 950                 955                 960

Tyr Ala Phe Lys Phe Glu Gln Pro Asp Leu Pro Leu Ala Asp Leu Ser
            965                 970                 975

Ser Gly Asn Gly Gly Gly Thr Gly Gly Gly Asp Thr Gly Gly Gly Thr
```

```
                    980             985             990
        Thr Glu Pro Gly Asp Val Val Glu Trp Val Pro Gly Ser Thr Gln Val
                995             1000            1005

Ser Asp Gly Thr Thr Val Thr Tyr Asn Gly Lys Cys Phe Val Ala Gln
            1010            1015            1020

Asn Ser Pro Gly Val Trp Glu Ser Pro Thr Gln Thr Asn Trp Phe Trp
        1025            1030            1035            1040

Glu Glu Val Thr Cys Pro
                    1045
```

(2) INFORMATION FOR SEQ ID NO:3:

(i) SEQUENCE CHARACTERISTICS:
        (A) LENGTH: 3670 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GGTGGTGGCA CCTCCTGCCG CGCGGTATTC GGCATGCGTC CGGCGTTTGA TTGGCGACAG     60

GACCGGCAGC GCCAACCTGT TGCTTGGCGT GGAACGCGAT GGACGCCGTC ATTCACGCCA    120

TCACCTTAGC TGCCGAACAA GGCGGCCTGA ATAACGATAA CTTTGGTCAA CTGCACGTGG    180

GCTTGGCGCT GGCTGGCGTG AGCACCAAGC GACTTGGCAT GCTTTATGCA ATTGCCACAC    240

CGTTTGCGTC GCTCACGCTC AATACCGATG CCTATGGTGC GTGCCTCGGT GCGCACCACG    300

GTGACAACGG CGCCATCATG ATTGCTGGCA CGGGCTCATG CGGTTTGTTC TTGCAAGACG    360

GCCACCAGCA CGTGGTGGGG GGACGTGAGT TCCCGATCTC CGATGAGGGC AGTGGCGCGG    420

TGATGGGACT GCGCCTGATT CAACAAGTGC TGCTGATTGA AGATGGTATT TATCCGGCCA    480

CGCCACTTAG TCAGTGTGTC ATGCAGCATT GACACGATGT GACGCCATTG TCGCTTGGTC    540

GAAATCCGCT TTACCTCGCG ACTATGGTCA ATTTTCGCCG CAGATTTTCG CGTTGGCGAA    600

TCAAGGTGAC ACGCTAGCAA TATCCCTGCT GAAACAGACA GCAGCGGATA TCGAAATGTT    660

TTTGAACGCC CTGCATCGCA AAGGGGCACA GCGAATCTGC TTCATGGGCA GCATCGCGGA    720

ACGCATTCAC GCATGGTTAT CCCCTCCCGT TCAGCAATGA ATCGTCGCAC CGCAAGCGGA    780

TGCGATGGAG GGCGCATTAA TGTTTGCCGG CAAAGCCGAG CATAATTTGT ATTAAGGGTT    840

GCTCATGAAC TATCGAATAG ACTTCGCGGT ATTGTCAGAA CATCCACAGT TCTGCCGTTT    900

TGGCTTGACG CTGCATAACC TCAGCGATCA GGACTTAAAG GCCTGGAGCC TGCATTTCAC    960

CATCGATCGC TACATTCAGC CCGATAGCAT CAGTCACAGC CAGATTCATC AAGTCGGCAG   1020

TTTCTGTTCG CTCACGCCGG AGCAGGACGT GATAAATTCC AACAGCCATT TCTACTGCGA   1080

ATTCAGCATC AAAACCGCGC CGTTTCCGTT TCACTATTAC ACCGACGGCA TCAAAGCCGC   1140

GTTTGTCCAA ATTAATGATG TAGAGCCGCG GGTTCGTCAC GACGTGATCG TCACCCCCAT   1200

CGCACTCGCC TCCCCCTATC GGGAACGCAG CGAGATCCCG GCCACGGATG CCGCGACGTT   1260

GAGCCTGTTA CCCAAACCCA ATCATATCGA ACGCTTGGAT GGTGAATTTG CCCTTACCGC   1320

CGGCAGCCAG ATTTCATTGC AATCCTCTTG TGCAGAAACT GCCGCCACGT GGCTCAAGCA   1380

AGAACTGACG CATCTCTATC AGTGGCAGCC ACACGATATT GGCAGCGCCG ACATTGTGCT   1440

ACGCACCAAC CCAACGCTGG ATGAAGGCGC CTATCTGCTG TCAGTCGACC GCAAACCTAT   1500

TCGTTTGGAA GCCAGCAGTC ACATCGGCTT TGTCCATGCC AGTGCGACAT TGCTGCAATT   1560

GGTTCGCCCA GATGGCGACA ACCTGCTGGT GCCACACATC GTTATCAAAG ACGCACCGCG   1620
```

-continued

```
CTTTAAATAC CGCGGCATGA TGCTGGATTG CGCGCGTCAT TTTCATCCGC TGGAGCGCGT    1680

TAAACGCCTC ATCAACCAAC TGGCGCATTA CAAATTCAAC ACCTTTCATT GGCATCTGAC    1740

CGATGATGAA GGTTGGCGCA TTGAAATTAA GTCTCTACCT CAATTGACCG ACATTGGCGC    1800

GTGGCGCGGT GTGGATGAAG TCCTGGAACC GCAATACAGC CTGCTGACCG AAAAACACGG    1860

TGGCTTTTAC ACCCAAGAGG AGATCCGTGA AGTGATCGCC TACGCCGCAG AACGCGGCAT    1920

CACGGTGATT CCAGAAATTG ACATTCCCGG TCACAGCCGA GCGGCGATCA AGCCTTACC     1980

GGAATGGCTA TTTGACGAAG ATGACCAATC ACAATACCGC AGCATTCAGT ACTACAACGA    2040

CAACGTGCTA TCGCCAGCCC TGCCCGGCAC CTACCGTTTT CTCGATTGCG TATTGGAGGA    2100

AGTGGCCGCG CTGTTTCCGA GCCATTTCAT TCACATTGGC GCCGATGAAG TGCCAGATGG    2160

CGTGTGGGTC AACAGCCCGA AATGTCAGGC ATTGATGGCA GAAGAGGGCT ACACCGACGC    2220

CAAAGAGTTA CAAGGGCACC TGCTGCGCTA TGCGGAGAAG AAGCTCAAAT CACTCGGCAA    2280

ACGCATGGTC GGTTGGGAAG AAGCGCAGCA TGGTGACAAA GTCAGCAAAG ATACCGTGAT    2340

TTATTCTTGG TTATCCGAAC AAGCCGCACT GAACTGCGCC CGTCAAGGGT TTGATGTCAT    2400

TTTACAACCG GGACAGTTTA CGTACCTCGA CATTGCGCAA GACTACGCGC CAGAAGAGCC    2460

GGGCGTCGAC TGGGCTGGCG TGACGCCACT GGAGCGCGCC TATCGCTACG AGCCGCTGGT    2520

CGAGGTGCCA GAACACGACC CGCTGCGCAA ACGCATTTTG GGGATTCAGT GCGCGCTGTG    2580

GTGTGAACTG GTCAACAATC AAGACCGCAT GGACTACATG ATCTATCCGC GTTTGACCGC    2640

ACTGGCGGGA AGCGGCTTGG ACACAAAAAT CCCAGCGTGA TTGGCTGGAT TACCTGGCGC    2700

GCCTCAAAGG CCATTTACCC CAACTTGATC AACAAGGCAT CCGCTACCGG GCGCCTTGGA    2760

AAGCATAACG CAACACGTTT TCTCTAGCAT CGACATTGAG TGGCGCCAAT GCGCCACTGT    2820

TTAAAAAGGA AATTACCATG AAATACGGCT ATTTCGATAA CGACAATCGC GAATACGTCA    2880

TTACTCGTCC CGATGTTCCT GCACCTTGGA CCAACTACCT CGGCACGGAA AAATTCTGCA    2940

CCGTCATCTC CCATAATGCG GGGGGCTACT CGTTCTATCA CTCACCCGAG TACAACCGTG    3000

TGACCAAGTT CCGTCCGAAC TTCACACAAG ATCGTCCCGG GCATTACATC TATTTGCGCG    3060

ATGATGAAAC CGGTGATTTC TGGTCGGTCT CTTGGCAGCC CGTTGCCAAA AACCTTGACG    3120

ATGCCCATTA CGAAGTGCGC CATGGATGCC GTGTATGAGT ATCTGTTCTC CCCATACGGT    3180

TTACACCTCA ACGCCCCCTC GTTTGCAACG CCCAACGATG ACATCGGTTT TGTCACCCGC    3240

GTCTACCAAG GCGTGAAAGA AAACGGTGCG ATTTTCTCGC ATCCGAACCC GTGGGCATGG    3300

GTCGCCGAAG CCAAACTGGG ACGCGGTGAT CGCGCGATGG AATTCTACGA TTCGCTCAAC    3360

CCATACAACC AGAACGACAT CATTGAAACG CGCGTGGCAG AGCCATATTC CTACGTGCAA    3420

TTCATCATGG GTCGCGACCA CCAAGATCAC GGCCGTGCAA ACCACCCTTG GCTCACCGGT    3480

ACATCGGGCT GGGCCTACTA CGCGACCACC AACTTCATTT TGGGAGTGCG TACCGGATTT    3540

GACAGGTTGA CCGTGGATCC ATGTATTCCT GCCGCTTGGT CGGGCTTTGA GCGTCACGCG    3600

CGAGTGGCGC GGTGCGACGT ATCACATGTC AGTCCAAAAC CCGAATGGCG TCAGCAAAGG    3660

CGTGCAATCG                                                          3670
```

(2) INFORMATION FOR SEQ ID NO:4:

(i) SEQUENCE CHARACTERISTICS:
        (A) LENGTH: 611 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Asn Tyr Arg Ile Asp Phe Ala Val Leu Ser Glu His Pro Gln Phe
1               5                   10                  15

Cys Arg Phe Gly Leu Thr Leu His Asn Leu Ser Asp Gln Asp Leu Lys
                20                  25                  30

Ala Trp Ser Leu His Phe Thr Ile Asp Arg Tyr Ile Gln Pro Asp Ser
            35                  40                  45

Ile Ser His Ser Gln Ile His Gln Val Gly Ser Phe Cys Ser Leu Thr
        50                  55                  60

Pro Glu Gln Asp Val Ile Asn Ser Asn Ser His Phe Tyr Cys Glu Phe
65                  70                  75                  80

Ser Ile Lys Thr Ala Pro Phe Pro Phe His Tyr Tyr Thr Asp Gly Ile
                85                  90                  95

Lys Ala Ala Phe Val Gln Ile Asn Asp Val Glu Pro Arg Val Arg His
                100                 105                 110

Asp Val Ile Val Thr Pro Ile Ala Leu Ala Ser Pro Tyr Arg Glu Arg
            115                 120                 125

Ser Glu Ile Pro Ala Thr Asp Ala Ala Thr Leu Ser Leu Leu Pro Lys
        130                 135                 140

Pro Asn His Ile Glu Arg Leu Asp Gly Glu Phe Ala Leu Thr Ala Gly
145                 150                 155                 160

Ser Gln Ile Ser Leu Gln Ser Ser Cys Ala Glu Thr Ala Ala Thr Trp
                165                 170                 175

Leu Lys Gln Glu Leu Thr His Leu Tyr Gln Trp Gln Pro His Asp Ile
            180                 185                 190

Gly Ser Ala Asp Ile Val Leu Arg Thr Asn Pro Thr Leu Asp Glu Gly
        195                 200                 205

Ala Tyr Leu Leu Ser Val Asp Arg Lys Pro Ile Arg Leu Glu Ala Ser
    210                 215                 220

Ser His Ile Gly Phe Val His Ala Ser Ala Thr Leu Leu Gln Leu Val
225                 230                 235                 240

Arg Pro Asp Gly Asp Asn Leu Leu Val Pro His Ile Val Ile Lys Asp
                245                 250                 255

Ala Pro Arg Phe Lys Tyr Arg Gly Met Met Leu Asp Cys Ala Arg His
            260                 265                 270

Phe His Pro Leu Glu Arg Val Lys Arg Leu Ile Asn Gln Leu Ala His
        275                 280                 285

Tyr Lys Phe Asn Thr Phe His Trp His Leu Thr Asp Asp Glu Gly Trp
    290                 295                 300

Arg Ile Glu Ile Lys Ser Leu Pro Gln Leu Thr Asp Ile Gly Ala Trp
305                 310                 315                 320

Arg Gly Val Asp Glu Val Leu Glu Pro Gln Tyr Ser Leu Leu Thr Glu
                325                 330                 335

Lys His Gly Gly Phe Tyr Thr Gln Glu Glu Ile Arg Glu Val Ile Ala
            340                 345                 350

Tyr Ala Ala Glu Arg Gly Ile Thr Val Ile Pro Glu Ile Asp Ile Pro
        355                 360                 365

Gly His Ser Arg Ala Ala Ile Lys Ala Leu Pro Glu Trp Leu Phe Asp
    370                 375                 380

Glu Asp Asp Gln Ser Gln Tyr Arg Ser Ile Gln Tyr Tyr Asn Asp Asn
385                 390                 395                 400

Val Leu Ser Pro Ala Leu Pro Gly Thr Tyr Arg Phe Leu Asp Cys Val
```

```
                        405                 410                 415
    Leu Glu Glu Val Ala Ala Leu Phe Pro Ser His Phe Ile His Ile Gly
                    420                 425                 430

Ala Asp Glu Val Pro Asp Gly Val Trp Val Asn Ser Pro Lys Cys Gln
                    435                 440                 445

Ala Leu Met Ala Glu Glu Gly Tyr Thr Asp Ala Lys Glu Leu Gln Gly
                    450                 455                 460

His Leu Leu Arg Tyr Ala Glu Lys Lys Leu Lys Ser Leu Gly Lys Arg
    465                 470                 475                 480

Met Val Gly Trp Glu Glu Ala Gln His Gly Asp Lys Val Ser Lys Asp
                    485                 490                 495

Thr Val Ile Tyr Ser Trp Leu Ser Glu Gln Ala Ala Leu Asn Cys Ala
                    500                 505                 510

Arg Gln Gly Phe Asp Val Ile Leu Gln Pro Gly Gln Phe Thr Tyr Leu
                    515                 520                 525

Asp Ile Ala Gln Asp Tyr Ala Pro Glu Glu Pro Gly Val Asp Trp Ala
                    530                 535                 540

Gly Val Thr Pro Leu Glu Arg Ala Tyr Arg Tyr Glu Pro Leu Val Glu
    545                 550                 555                 560

Val Pro Glu His Asp Pro Leu Arg Lys Arg Ile Leu Gly Ile Gln Cys
                    565                 570                 575

Ala Leu Trp Cys Glu Leu Val Asn Asn Gln Asp Arg Met Asp Tyr Met
                    580                 585                 590

Ile Tyr Pro Arg Leu Thr Ala Leu Ala Gly Ser Gly Leu Asp Thr Lys
                    595                 600                 605

Ile Pro Ala
        610
```

(2) INFORMATION FOR SEQ ID NO:5:

(i) SEQUENCE CHARACTERISTICS:
        (A) LENGTH: 1713 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GTACCCTCGA CGCCGTCCAT GCTGGTGCCG GACATGATGC CGATGTACAG TTCGCGTTCA      60

GTCATTCTGT TATCCGATTG TCATATTTCT CGTTTCCGAG GGCGAAGTCT TTAAAACTCA     120

TTGTAATTGA AAAACAAACT GAATAACCTC ATTTGCTGTG ACAAATTTTG ACAATCCACC     180

GTGATGAATG AAGGGGAAAA CATGGGACCG TTATGGCTAG ACGTTGAAGG TTGTGAACTG     240

ACGGCGGAAG ACCGCGAAAT ACTGGCGCAT CCTACCGTTG GCGGTGTCAT TTTGTTTGCT     300

CGTAACTACC ACGACAACCA ACAATTATTG GCGCTGAACA CCGCCATTCG TCAGGCGGCG     360

AAGCGCCCGA TCCTGATTGG GGTGGATCAA GAAGGTGGCC GCGTGCAGCT TTCGCGACGG     420

GTTCAGCAAG ATCCCTGCGC GCAGCTTTAT GCGCGCAGCG ACAATGGTAC GCAGTTGGCC     480

GAAGACGGCG GCTGGTTGAT GGCGGCGGAA CTCATCGCAC ACGACATTGA TCTCAGCTTT     540

GCGCCCGTAT TGGATAAGGG TTTTGATTGC CGTGCAATTG GCAACCGCGC CTTTGGTGAC     600

GATGTGCAAA CCGTGTTGAC CTATAGCAGC GCCTATATGC GCGGCATGAA ATCTGTGGGG     660

ATGGCGACCA CCGGCAAACA CTTTCCCGGT CACGGTGCGG TGATTGCCGA CTCCCATCTG     720

GAAACGCCTT ACGATGAACG TGATTCGATT GCTGACGACA TGACGATTTT CCGCGCGCAG     780
```

```
ATTGAAGCGG GCATTTTGGA TGCCATGATG CCTGCGCACG TGATTTATCC GCACTATGAT    840

GCCCAGCCCG CCAGCGGCTC TCCGTATTGG CTGAAACAGG TTTTGCGTCA GGAACTGGGC    900

TTTCAAGGCA TCGTGTTCTC GGATGATTTG AGCATGGAAG GTGCGGCGAT CATGGGCGGC    960

CCGGCAGAGC GTGCGCAGCA GTCGCTGGAT GCCGGTTGCG ACATGGTGCT GATGTGCAAC   1020

AAGCGCGAAT CGGCAGTCGC GGTGTTGGAT CAGCTACCAA TCAGTGTGGT GCCGCAAGCG   1080

CAGTCGCTGC TGAAACAGCA ACAGTTCACC TACCGTGAAC TGAAAGCGAC TGAGCGTTGG   1140

AAGCAGGCGT ATCAAGCGCT GCAGCGTTTG ATTGACGCGC ACAGCTAACG GCACATTCGC   1200

GATCAAGAAA GGCTCCCATG GGAGCCTTTT GTCAATGCAG CGATTTTGCG GCCAACGGTT   1260

AGTGGAAGCC CAATTTCTCT TTTAGTTCTT TGAGGTAACG GCGACTGACG GGACTTGAT    1320

GGCCGGAGCG GGTGATGATC TCCGCCAACC CGTTTTCCAA CAGTTTGATT TCTTTGATCG   1380

CTTTGGTGTT CACCAGATAC TGGCGATGGC AGCGCACCAA CGGCGTTTTC TCTTCCAAAA   1440

TTTTGAGCGT CAACTGGCTG GTGGCGCGTT GCTGATGGGT TTGTACGTGC ACGCCGCTGA   1500

TGTCGCTAAA CGCAAACTCC ACATCGACTG TCGGTACAAT CACAATGCGG TTCAGGCCAA   1560

TGCATGGCAC CTGATCCAGA TTATTTGGCG CTAGGGCGGA GTAGTCTTGC GTCTTGTTCA   1620

CGCTGCGCCC AAGCGTTGG ATGGTTTTTT CCAACCTTGC CGGGTCAATC GGCTTGAGCA    1680

GGTAATCAAA CGCATTGTCT TCAAAGCCTT GCA                                1713

(2) INFORMATION FOR SEQ ID NO:6:

(i) SEQUENCE CHARACTERISTICS:
        (A) LENGTH: 328 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Met Gly Pro Leu Trp Leu Asp Val Glu Gly Cys Glu Leu Thr Ala Glu
        1               5                   10                  15

Asp Arg Glu Ile Leu Ala His Pro Thr Val Gly Val Ile Leu Phe
                    20                  25                  30

Ala Arg Asn Tyr His Asp Asn Gln Gln Leu Leu Ala Leu Asn Thr Ala
                    35                  40                  45

Ile Arg Gln Ala Ala Lys Arg Pro Ile Leu Ile Gly Val Asp Gln Glu
        50                  55                  60

Gly Gly Arg Val Gln Leu Ser Arg Arg Val Gln Gln Asp Pro Cys Ala
        65                  70                  75                  80

Gln Leu Tyr Ala Arg Ser Asp Asn Gly Thr Gln Leu Ala Glu Asp Gly
                        85                  90                  95

Gly Trp Leu Met Ala Ala Glu Leu Ile Ala His Asp Ile Asp Leu Ser
                    100                 105                 110

Phe Ala Pro Val Leu Asp Lys Gly Phe Asp Cys Arg Ala Ile Gly Asn
                    115                 120                 125

Arg Ala Phe Gly Asp Asp Val Gln Thr Val Leu Thr Tyr Ser Ser Ala
                    130                 135                 140

Tyr Met Arg Gly Met Lys Ser Val Gly Met Ala Thr Thr Gly Lys His
        145                 150                 155                 160

Phe Pro Gly His Gly Ala Val Ile Ala Asp Ser His Leu Glu Thr Pro
                        165                 170                 175

Tyr Asp Glu Arg Asp Ser Ile Ala Asp Asp Met Thr Ile Phe Arg Ala
                    180                 185                 190
```

```
       Gln Ile Glu Ala Gly Ile Leu Asp Ala Met Met Pro Ala His Val Ile
           195                 200                 205

Tyr Pro His Tyr Asp Ala Gln Pro Ala Ser Gly Ser Pro Tyr Trp Leu
           210                 215                 220

Lys Gln Val Leu Arg Gln Glu Leu Gly Phe Gln Gly Ile Val Phe Ser
       225                 230                 235                 240

Asp Asp Leu Ser Met Glu Gly Ala Ala Ile Met Gly Gly Pro Ala Glu
                       245                 250                 255

Arg Ala Gln Gln Ser Leu Asp Ala Gly Cys Asp Met Val Leu Met Cys
                   260                 265                 270

Asn Lys Arg Glu Ser Ala Val Ala Val Leu Asp Gln Leu Pro Ile Ser
                   275                 280                 285

Val Val Pro Gln Ala Gln Ser Leu Leu Lys Gln Gln Gln Phe Thr Tyr
           290                 295                 300

Arg Glu Leu Lys Ala Thr Glu Arg Trp Lys Gln Ala Tyr Gln Ala Leu
       305                 310                 315                 320

Gln Arg Leu Ile Asp Ala His Ser
                       325
```

(2) INFORMATION FOR SEQ ID NO:7:

(i) SEQUENCE CHARACTERISTICS:
        (A) LENGTH: 2951 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
TGTTGTCTGC GTTACCTGTC CGGTCGCGTT GCCTTTTTCG TTGTTCATAC CAATAACGAA      60

ATAAGGAAGT TCAACTATGT TCAGTCCAAA ACATTCCCTG CTGGCATTGC TGGTCGGGGG     120

GCTCTGTTCT ACCTCCGCCC TCGCTGCCGC CCCCGGCAAA CCCACCATCG GCTGGGGTGA     180

AACCAAGTTC GCCATCATCC AGGTCGATCA GGCCGCCACC TCCTACAACA AGCTGGTCAC     240

TGTCCACAAG GACGGCGCCC CGGTCAGCGT GACCTGGAAC CTCTGGTCCG GCGATGTGGG     300

CCAGACCGCC AAGGTACTGC TCGATGGCAA GGAAGTCTGG TCCGGCGCCG CCAGTGCGGC     360

GGGCACCGCC AACTTCAAGG TCACCAAGGG TGGCCGCTAT CAGATGCAGG TGGCCCTGTG     420

CAACGCCGAC GGCTGCACCC TATCCGACAA GAAGGAGATA GTGGTGGCCG ACACGGACGG     480

CAGCCACCTG GCGCCGCTCA ATGCGCCCCT GCAAGAGAAC AACAAGCCTT ACACCAACAA     540

GGCCGGCAAG GTGGTCGGGG CCTACTACGT GGAGTGGGGC GTCTATGGCC GCAAGTTCAC     600

CGTGGACAAG ATCCCGGCCA AGAACCTGAC CCACATCCTC TATGGCTTCA CCCCCATCTG     660

TGGCGGTAAC GGCATCAACG ACAGCCTGAA AGAGATCTCA GGCAGCTTCG AGGCACTGCA     720

GCGCTCCTGC GCCGGCCGTG AGGACTTCAA GGTCTCCATC CATGATCCCT GGGCCGCGGT     780

CCAGATGGGG CAGGGCAATC TCACCGCCTT CGACGAGCCC TACAAGGGCA ACTTCGGCAA     840

CCTGATGGCG CTGAAGAAAG CCAACCCAAA CCTCAAGATC CTGCCTTCCG TGGGTGGCTG     900

GACCCTGTCC GACCCCTTCT ACTTCTTCAG TGACAAGACC AAGCGCGACA CCTTCGTCGC     960

CTCCATGAAG GAGTACCTGC AGACCTGGAA ATTCTTCGAT GGCGTGGACA TCGACTGGGA    1020

GTTCCCGGGT GGCCAGGGTG CCAACCCCAA TCTGGGTGGC CCGAACGATG GCGCCACCTA    1080

TGTGGCCCTG ATGAAAGAGC TGCGCGCCAT GCTGGACGAG CTGGAAGCCG AGACCGGCCG    1140

CCAGTATGAG CTCACCTCGG CCATCAGCGC CGGCGGCGAC AAGATTGCCA AGGTGGACTA    1200
```

```
TCAGGCTGCC CAGCAGTACA TGGATTACAT CTTCCTGATG AGCTACGACT TCAGCGGCGC    1260

CTTCGATCTG AAGAACCTGG CTCACCAGAC CAACCTCTAT GCATCAAGCT GGGATCCGGC    1320

CACCAAGTAC ACCACCGACA AGGGCGTCAA GGCGCTGCTC GGCCAGGGTG TGACTCCGGG    1380

CAAGGTCGTG GTCGGTGCGG CCATGTATGG CCGTGGCTGG ACCGGGGTCA ATGGCTATCA    1440

GGCCGGCAAC CCCTTCACCG GCAGTGCGAC CGGTCCCATC AAGGGCACCT GGGAGAATGG    1500

CGTGGTGGAT TACCGCGATA TCGTCAACAA CCGCATGGGC GCGGGCTGGG AGCAGGGCTA    1560

TGACGAAACG GCGGAAGCGC CTTACGTCTT CAAGGCGAGC ACCGGCGATC TCATCAGCTT    1620

CGACAACGAT CGCTCGGTCA AGGCCAAGGG GCAGTACGTG CTGGCCAACC AGCTCGGCGG    1680

CCTGTTCGCC TGGGAGATCG ATGCGGATAA CGGCGACATC TTGAACGCCA TGCACGAAGG    1740

GCTCGGCAAC GGGGACGGCG GCACCACGCC ACCGGTCAAC AAGCCGCCCG TGGCCAATGC    1800

AGGTAGCGAT CTGAGCGACA CAGGCCCGGC CGAGGTGACC CTCAACGGCG CCGCCTCCCA    1860

TGACCCCGAG AGCGGTGTGC TGAGCTACAG CTGGAAGCAG GTCTCTGGCC CGCAGGTCAG    1920

CCTGCTCGAT GCTACTCAGG CCAAGGCCCG GGTAGTGTTG GACGCCGTCA GCGCCGACAT    1980

CAACCTGGTG TTCGAGCTGA CCGTCACCGA CGATCACAAC CTCACGGCCA AGGATCAGGT    2040

GGTGGTGACC AACAAGGCGC CGCAGCCTAA CCTGCCGCCC GTAGTGACGG TACCGGCCAC    2100

CGCCAGCGTC GAATCCGGCA AGCAGGTGAC CATCAAGGCC ACCGCCTCCG ATCCGAACGG    2160

CGACGCCCTG ACCTATCAGT GGAGCCTGCC TGCGGGTCTC ACCGCCACCG GTCAGAACAG    2220

CGCGACCCTG GTAGTCACAG GCCCGAGCGT CACCAGCGAC ACCGCCTATG ACCTGAGCCT    2280

GGTGGTCACC GACGGCTCTC TGGATGCCAG TGCCGGCACC CGTCTGACCG TCAAACCGGC    2340

GAGCACTGGG GGTGGCTGTG AGGCAACCGA TCCGGATGCG GCCAACCACC CGGCCTGGAG    2400

CGCCAGCGCC GTCTACAACA CCAATGCCAA GGTGAGCCAC AAGCAGCTAG TGTGGCAAGC    2460

CAAGTATTGG ACCCAGGGCA ACGAGCCAAG CCAGACCGCG GATCAGTGGA AGCTGCTGAG    2520

TGCGGTGCAG CTCGGCTGGA ATGCCGGGGT GGCCTATAAC GCCGGCGACC TGACCAACCA    2580

CAACGGTCGC AAGTGGAAGG CCCAGTACTG GACCAAGGGT GACGAGCCCG GCAAGGCCGC    2640

CGTCTGGGTT GACCAGGGTG CTGCCAGCTG TAACTGAGTG ACATCATGAC CAAGCAATG     2700

GGGCCCGGTG CCCCATTGCT TTCTCCACCC ACCTTCCCGA CCTGCCAGAT ATTCCCAATC    2760

TGCTATCAGA ACGTCGTACA TCAGCGCTAT GCGCACCGAG GATATTTTCA ATGCACCAAG    2820

ACAGCACGCA GTGGATGGGC AAACTCTCCA TCCTGGGGCT GGCGATCCTG AATATCAGCC    2880

CGCTGGCGAT GGCTCAACAG AGCAGCACGA CCGGCGAGTT TCGCAAAGAC AACAGCGCTC    2940

CCCAGATCCC C                                                        2951
```

(2) INFORMATION FOR SEQ ID NO:8:

(i) SEQUENCE CHARACTERISTICS:
        (A) LENGTH: 866 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Phe Ser Pro Lys His Ser Leu Leu Ala Leu Leu Val Gly Gly Leu
 1               5                  10                  15

Cys Ser Thr Ser Ala Leu Ala Ala Pro Gly Lys Pro Thr Ile Gly
                 20                  25                  30
```

-continued

```
Trp Gly Glu Thr Lys Phe Ala Ile Ile Gln Val Asp Gln Ala Ala Thr
         35                  40                  45
Ser Tyr Asn Lys Leu Val Thr Val His Lys Asp Gly Ala Pro Val Ser
 50                  55                  60
Val Thr Trp Asn Leu Trp Ser Gly Asp Val Gly Gln Thr Ala Lys Val
 65                  70                  75                  80
Leu Leu Asp Gly Lys Glu Val Trp Ser Gly Ala Ala Ser Ala Ala Gly
                 85                  90                  95
Thr Ala Asn Phe Lys Val Thr Lys Gly Gly Arg Tyr Gln Met Gln Val
                100                 105                 110
Ala Leu Cys Asn Ala Asp Gly Cys Thr Leu Ser Asp Lys Lys Glu Ile
            115                 120                 125
Val Val Ala Asp Thr Asp Gly Ser His Leu Ala Pro Leu Asn Ala Pro
    130                 135                 140
Leu Gln Glu Asn Asn Lys Pro Tyr Thr Asn Lys Ala Gly Lys Val Val
145                 150                 155                 160
Gly Ala Tyr Tyr Val Glu Trp Gly Val Tyr Gly Arg Lys Phe Thr Val
                165                 170                 175
Asp Lys Ile Pro Ala Lys Asn Leu Thr His Ile Leu Tyr Gly Phe Thr
                180                 185                 190
Pro Ile Cys Gly Gly Asn Gly Ile Asn Asp Ser Leu Lys Glu Ile Ser
            195                 200                 205
Gly Ser Phe Glu Ala Leu Gln Arg Ser Cys Ala Gly Arg Glu Asp Phe
    210                 215                 220
Lys Val Ser Ile His Asp Pro Trp Ala Ala Val Gln Met Gly Gln Gly
225                 230                 235                 240
Asn Leu Thr Ala Phe Asp Glu Pro Tyr Lys Gly Asn Phe Gly Asn Leu
                245                 250                 255
Met Ala Leu Lys Lys Ala Asn Pro Asn Leu Lys Ile Leu Pro Ser Val
                260                 265                 270
Gly Gly Trp Thr Leu Ser Asp Pro Phe Tyr Phe Phe Ser Asp Lys Thr
            275                 280                 285
Lys Arg Asp Thr Phe Val Ala Ser Met Lys Glu Tyr Leu Gln Thr Trp
    290                 295                 300
Lys Phe Phe Asp Gly Val Asp Ile Asp Trp Glu Phe Pro Gly Gly Gln
305                 310                 315                 320
Gly Ala Asn Pro Asn Leu Gly Gly Pro Asn Asp Gly Ala Thr Tyr Val
                325                 330                 335
Ala Leu Met Lys Glu Leu Arg Ala Met Leu Asp Glu Leu Glu Ala Glu
                340                 345                 350
Thr Gly Arg Gln Tyr Glu Leu Thr Ser Ala Ile Ser Ala Gly Gly Asp
            355                 360                 365
Lys Ile Ala Lys Val Asp Tyr Gln Ala Ala Gln Gln Tyr Met Asp Tyr
    370                 375                 380
Ile Phe Leu Met Ser Tyr Asp Phe Ser Gly Ala Phe Asp Leu Lys Asn
385                 390                 395                 400
Leu Ala His Gln Thr Asn Leu Tyr Ala Ser Ser Trp Asp Pro Ala Thr
                405                 410                 415
Lys Tyr Thr Thr Asp Lys Gly Val Lys Ala Leu Leu Gly Gln Gly Val
                420                 425                 430
Thr Pro Gly Lys Val Val Gly Ala Ala Met Tyr Gly Arg Gly Trp
            435                 440                 445
Thr Gly Val Asn Gly Tyr Gln Ala Gly Asn Pro Phe Thr Gly Ser Ala
    450                 455                 460
```

```
Thr Gly Pro Ile Lys Gly Thr Trp Glu Asn Gly Val Val Asp Tyr Arg
465                 470                 475                 480

Asp Ile Val Asn Asn Arg Met Gly Ala Gly Trp Glu Gln Gly Tyr Asp
                485                 490                 495

Glu Thr Ala Glu Ala Pro Tyr Val Phe Lys Ala Ser Thr Gly Asp Leu
            500                 505                 510

Ile Ser Phe Asp Asn Asp Arg Ser Val Lys Ala Lys Gly Gln Tyr Val
        515                 520                 525

Leu Ala Asn Gln Leu Gly Gly Leu Phe Ala Trp Glu Ile Asp Ala Asp
    530                 535                 540

Asn Gly Asp Ile Leu Asn Ala Met His Glu Gly Leu Gly Asn Gly Asp
545                 550                 555                 560

Gly Gly Thr Thr Pro Pro Val Asn Lys Pro Val Ala Asn Ala Gly
                565                 570                 575

Ser Asp Leu Ser Asp Thr Gly Pro Ala Glu Val Thr Leu Asn Gly Ala
            580                 585                 590

Ala Ser His Asp Pro Glu Ser Gly Val Leu Ser Tyr Ser Trp Lys Gln
        595                 600                 605

Val Ser Gly Pro Gln Val Ser Leu Leu Asp Ala Thr Gln Ala Lys Ala
    610                 615                 620

Arg Val Val Leu Asp Ala Val Ser Ala Asp Ile Asn Leu Val Phe Glu
625                 630                 635                 640

Leu Thr Val Thr Asp Asp His Asn Leu Thr Ala Lys Asp Gln Val Val
                645                 650                 655

Val Thr Asn Lys Ala Pro Gln Pro Asn Leu Pro Pro Val Val Thr Val
            660                 665                 670

Pro Ala Thr Ala Ser Val Glu Ser Gly Lys Gln Val Thr Ile Lys Ala
        675                 680                 685

Thr Ala Ser Asp Pro Asn Gly Asp Ala Leu Thr Tyr Gln Trp Ser Leu
    690                 695                 700

Pro Ala Gly Leu Thr Ala Thr Gly Gln Asn Ser Ala Thr Leu Val Val
705                 710                 715                 720

Thr Gly Pro Ser Val Thr Ser Asp Thr Ala Tyr Asp Leu Ser Leu Val
                725                 730                 735

Val Thr Asp Gly Ser Leu Asp Ala Ser Ala Gly Thr Arg Leu Thr Val
            740                 745                 750

Lys Pro Ala Ser Thr Gly Gly Gly Cys Glu Ala Thr Asp Pro Asp Ala
        755                 760                 765

Ala Asn His Pro Ala Trp Ser Ala Ser Ala Val Tyr Asn Thr Asn Ala
    770                 775                 780

Lys Val Ser His Lys Gln Leu Val Trp Gln Ala Lys Tyr Trp Thr Gln
785                 790                 795                 800

Gly Asn Glu Pro Ser Gln Thr Ala Asp Gln Trp Lys Leu Leu Ser Ala
                805                 810                 815

Val Gln Leu Gly Trp Asn Ala Gly Val Ala Tyr Asn Ala Gly Asp Leu
            820                 825                 830

Thr Asn His Asn Gly Arg Lys Trp Lys Ala Gln Tyr Trp Thr Lys Gly
        835                 840                 845

Asp Glu Pro Gly Lys Ala Ala Val Trp Val Asp Gln Gly Ala Ala Ser
    850                 855                 860

Cys Asn
865
```

BACTERIAL CATABOLISM OF CHITIN

This application is a continuation-in-part of U.S. Ser. No. 08/386,727, filed on Feb. 13, 1995.

This patent application was supported in part by grants N00014-91-J-4033, N00014-92-J-1936 and N00014-93-1-0630 from the Office of Naval Research and grant 5 R37 GM38759 from the National Institutes of Health. The Government has certain rights in the invention.

BACKGROUND OF THE INVENTION

1. Field of the Invention

The present invention is in the general field of the catabolic pathway of chitin and generally relates to genes encoding enzymes for cleaving chitin into its component parts.

2. Description of the Related Art

At least 18 species of Vibrionaceae are chitinolytic. Six are human pathogens, including *V. furnissii*, *V. cholerae* and *V. parahaemolyticus*. A brief review (1) entitled "Cholera, Copepods, and Chitinase" describes the relationships between the Vibrios, zooplankton, annual cycles of the bacteria, the invertebrates, and human disease such as food poisoning and endemic cholera. One important element in the epidemiology (2) is that *V. cholerae* adhering to chitin particles are protected from acid (equivalent to the stomach acid barrier) which kills almost all of the free-living organisms. This protection is explained by the fact that virtually all of the microbes in zooplankton "burrow" into the organism, and are not exposed to the medium (3).

Chitin and chitosan are commercial products used (especially in Japan) in medicine, agriculture, and for waste and water treatment. The polymers are used as wound dressing synthetic skin, drug delivery systems, sutures, to make contact lenses, as anticholesteremic agents, bactericidal agents, etc. (4). Chitin sutures are slowly degraded by lysozyme, and eventually absorbed, although nothing is known of the fate of the products, $(GlcNAc)_n$. $(GlcNAc)_6$ is claimed to be a potent anti-metastatic agent against mouse bearing Lewis lung carcinoma, and $(GlcNAc)_n$ activate macrophages and the immune system.

Although chitinase activities were recognized early in this century (5), the first reports on the stepwise enzymatic degradation of the polymer appear to be those of Zechmeister and Toth (6) who chromatographed extracts of almond emulsin, and of the snail, *Helix pomatia*, and separated an exo and an endoenzyme from each. The chitinase or "polysaccharidase" converted particulate chitin to the disaccharide, N,N'-diacetylchitobiose, $(GlcNAc)_2$, and the "chitobiase," or β-N-acetylglucosaminidase (β-GlcNAcidase), hydrolyzed the disaccharide to GlcNAc. Chitin degradation continues to be intensively studied (4,5, 7). Chitinases and chitobiases are found in bacteria, fungi, plants, and animals (vertebrates and invertebrates). The structural genes encoding a number of these enzymes and some of their regulatory regions have been cloned and sequenced (5,8–21). These data show that some organisms are capable of expressing multiple chitinases, but the pathway of chitin degradation is essentially the same as that proposed in the original studies (6), i.e., virtually all investigators agree that only two enzymes are required to degrade chitin to GlcNAc (5,7). The results of the present invention with *Vibrio furnissii* differ markedly from this concept. This organism not only expresses unique hexosaminidases, but we estimate that more than two dozen proteins are required for utilization of the polysaccharide (conversion to GlCNAc-6-P).

Despite early interest in chitin utilization by marine bacteria, there are few reports on the pathway in these organisms. A chitinase gene was cloned from *Aeromonas hydrophila* (an aquatic bacterium) into *E. coli* (22); the enzyme is normally secreted by the Aeromonas into the medium, but in the transformant it traversed only the inner membrane. Zyskind et al. (23,24) cloned the β-GlcNAcidase gene from *V. harveyi* into *E. coli*, found that it was transported to the outer membrane after cleavage of a signal sequence, and that the gene sequence was similar to that of the α-chain of human β-hexosaminidase (5). In *V. harveyi*, the β-GlcNAcidase is induced by $(GlcNAc)_2$. A β-GlcNAcidase gene has also been cloned from *V. vulnificus* (25), and these researchers suggest that this single enzyme is responsible for the complete degradation of chitin to GlcNAc, although the *E. coli* transformant is unable to clear chitin on chitin/agar plates. The chitobiase gene from *V. parahaemolyticus* was cloned into *E. coli* and the enzyme purified to homogeneity (26). The purified preparation showed four closely stacked bands, which the authors speculate may result from post-translational processing at the C-terminus; the hexosaminidase was active over the pH range 4–10. Laine also reports in an Abstract from a recent meeting (27) that his laboratory has cloned a chitinase gene from *V. parahaemolyticus*; the chitinase is secreted by the *E. coli* transformant.

While chitin and chitosan have been used commercially for various purposes for many years (4), the respective oligosaccharides have only recently been shown to be physiologically active. Chitin oligosaccharides (derivatized at the non-reducing end with a fatty acyl group) are signals generated by the soil bacterial genus Rhizobium, and recognized by host leguminous plants so that nitrogen fixing nodules are formed (51). Chitosan and chitin oligosaccharides induce pisatin and as many as 20 disease resistance response proteins in pea tissue and inhibit the growth of some fungal pathogens. GlcNAc and $(GlcNAc)_2$ were inactive, the trimer was slightly active, and the tetramer and pentamer were moderately active, both as antifungicides and pisatin elicitors (52,53). $(GlcNAc)_6$ is a potent antimetastatic agent against mouse bearing Lewis lung carcinoma, and $(GlcNAc)_n$ activate macrophages and the immune system (13). The disaccharide, $(GlcNAc)_2$ is linked to the amide group of asparagine in a large number of glycoproteins, such as those found in the blood. The disaccharide is the core to which the oligosaccharide chains of these glycoproteins are attached. Enzymes that hydrolyze the glycoprotein or glycopeptides by splitting the disaccharide (e.g., Endo A and H) or the asparagine amide (releasing the oligosaccharide) are of considerable commercial significance since they are useful for analysis and structure determination of these important macromolecules.

It is important to emphasize that the plant defense mechanisms are induced by the elicitor oligosaccharides. The multitude of proteins in the *V. furnissii* chitin catabolic cascade are likewise induced, and induction is differential. That is, higher $(GlcNAc)_n$ oligomers induce the extracellular chitinases, $(GlcNAc)_2$ induces a large number of proteins required for its catabolism but not the chitinases, and GlcNAc induces those proteins required for its metabolism but not the others. More importantly for present purposes, GlcNAc represses expression of the enzymes induced by $(GlcNAc)_2$ even when the latter is present in the medium, and $(GlcNAc)_2$ appears to repress expression of the chitinases. The biological activities of chitin and chitosan oligosaccharides may be expressed by individual oligomers, but not by mixtures of oligomers, especially by mixtures containing the lower molecular weight oligosaccharides.

The oligosaccharides have use in agriculture (e.g., to induce disease resistance) and in medicine. The costs of the commercially available oligosaccharides are prohibitive. While practical grade chitin costs from $22–49 per kilogram, the pure oligosaccharides cost from $5/mg (for $(GlcNAc)_2$) to about $15/mg (for $(GlcNAc)_6$). The problem can be illustrated with one example. $(GlcNAc)_2$ induces a large number of important proteins and enzymes in *V. furnissii*, whereas $(GlcNAc)_5$ and $(GlcNAc)_6$ induce others (48). The minimum concentration of $(GlcNAc)_2$ required for maximum induction is 0.6 mM in the growth medium (containing lactate or glycerol to spare the disaccharide). Thus, 0.6 mM $(GlcNAc)_2$ for one liter of medium would cost $1,270 and yield about 250 mg of induced cells (dry weight) and a few μg of each enzyme. For the experiments involving $(GlcNAc)_6$ at 0.6 mM, the cost would be $11,000 per liter!

The procedure for making these oligomers explains their cost. The first method for isolating chitosan oligomers was developed in the laboratory of the present inventors (54), as well as the method for their quantitative N-acetylation (55,56). The same methods are still being used commercially as indicated in the Seikagaku America, Inc., catalogue. Briefly, the procedure is as follows: purified chitin is completely deacetylated by fusion with KOH pellets under $N_2$, giving chitosan. The latter is purified by "recrystallization" 12 times to remove colored impurities, and partially hydrolyzed in 10.5N HCl at 53° C. for 72 h. The hydrolysate is applied to an ion-exchange column and eluted with a 0 to 4.2M HCl gradient. In this procedure, 5 g of chitosan were used, the ion exchange column contained 1 liter of resin, and 500 ml fractions were collected (total volume, 60 liters!). While the resolution from monomer to at least the pentamer was very good, it is obvious that the method is very limited with respect to quantity. For example, 244 mg of $(GlcNH_2)_5$ were obtained. Following quantitative N-acetylation with acetic anhydride, this quantity of material is sufficient for one 400 ml *V. furnissii* induction/growth experiment of the type described above.

The major problem in isolating large quantities of pure oligosaccharides are the limitations in resolving mixtures of these compounds. Even E-chitinase, which hydrolyzes chitin primarily to $(GlcNAc)_2$, yields significant quantities of GlcNAc. Wild type and genetically engineered *V. furnissii* and *E. coli* cells are used to remove contaminants. The lower six carbon atoms of sialic acid have the configuration of N-acetylmannosamine (not previously recognized as a natural sugar), not GlcNAc as reported (57–59). To study the metabolism, especially the enzymatic synthesis of sialic acid, requires substrate quantities of N-acetylmannosamine (ManNAc). The chemical synthesis of ManNAc is tedious and gives small amounts of material. The problem was solved (60) by alkaline epimerization of 25 to 100 g quantities of N-acetylglucosamine; the equilibrium mixture contained 80% GlcNAc and 20% ManNAc. Part of the GlcNAc crystallized when the solution was concentrated, and the remainder (5 to 20 g, depending on the scale) was removed with *E. coli* cells induced to catabolize GlcNAc. To illustrate the power of the method, 200 mg of *E. coli* cells (dry weight) obtained from 1 liter of culture were sufficient to completely remove all of the GlcNAc from the 25 g GlcNAc epimerization mixture in 4 h at 37° C. After the incubation, the mixture was deproteinized with $Ba(OH)_2$ and $ZnSO_4$, deionized, and pure ManNAc crystallized from the concentrated supernatant fluid in 70% yield (3.5 g of the 5 g formed in the epimerization reaction). Yields up to 80% were obtained from the 100 g reaction. In studies on the physical properties of the periplasmic space in *E. coli* and *Salmonella typhimurium* (61), it was necessary to remove traces of glucose and fructose from commercial (labeled and unlabeled) sucrose. The same methodology was successfully employed.

The preparation of the chitin oligosaccharides is based on similar procedures, i.e., a combination of partial hydrolysis of chitin to yield a mixture of soluble oligomers, followed by treatment with appropriate enzymes and/or mutant or transformed cells to resolve the mixtures and to obtain single products, or of desired mixtures, such as $(GlcNAc)_4$ and $(GlcNAc)_5$.

SUMMARY OF THE INVENTION

The present invention discloses the cloning of the genes that encode three β-N-acetylglucosaminidases involved in the catabolism of chitin in *Vibrio furnissii*. The functions of these enzymes in the chitin catabolic pathway are illustrated in FIG. 1. The relevant three genes are, endI which encodes periplasmic chitodextrinase (Endo-I), exoI which encodes periplasmic β-GlcNAcidase (Exo-I) and exoII which encodes an enzyme, aryl β-N-acetylglucosaminidase, specific for aryl β-N-acetylglucosaminides (Exo-II). In one aspect of the present invention, the complete nucleotide sequences for the chiA, the endI, the exoI, and the exoII genes from *V. furnissii* are disclosed.

In another aspect of the present invention, the complete amino acid sequences for the periplasmic chitodextrinase (Endo-I), the periplasmic β-N-acetylglucosaminidase (Exo-I), and an aryl β-N-acetylglucosaminidase (Exo-II) are disclosed.

In a further aspect of the present invention, host cells transformed with the endI gene and capable of expressing recombinant periplasmic chitodextrinase, host cells transformed with the exoI gene and capable of expressing recombinant periplasmic β-GlcNAcidase, and host cells transformed with the exoII gene and capable of expressing recombinant aryl β-N-acetylglucosaminidase are disclosed.

In another aspect of the present invention, four specific strains of *V. furnissii* having deletions in genes involved in the catabolic pathway of chitin are disclosed. More specifically, strains of *V. furnissii* having specific mutations in either the endI or the exoI genes are disclosed.

In another aspect of the present invention, a novel process for the production of specific chitin oligosaccharides is disclosed. This process involves the use of the recombinant enzymes, *E. coli* transformants and *V. furnissii* deletion mutants listed above.

DETAILED DESCRIPTION OF THE PREFERRED EMBODIMENTS

The cloning of each of the three genes from *V. furnissii*, the characterization of each isolated gene, the transformation of host cells with each isolated gene and the characterization of each recombinant β-N-acetylglucosaminidase follow. The next section (General Methods) gives details of procedures that were used for the isolation and characterization of all of the genes, while the section that follows (Specific Methods) gives specific details for each of the genes and enzymes.

The present invention relates to the isolation and characterization of genes involved in the catabolic pathway of chitin in *Vibrio furnissii*. More specifically, the present invention relates to the cloning of genes for four β-N-acetylglucosaminidases, one endo- and two exoenzymes:

endI encodes an endoenzyme, periplasmic chitodextrinase, or Endo-I, exoI encodes an exoenzyme, periplasmic β-N-acetylglucosaminidase or Exo-I and exoII encodes an exoenzyme, an aryl β-N-acetylglucosaminidase, or Exo-II.

Figure 1:
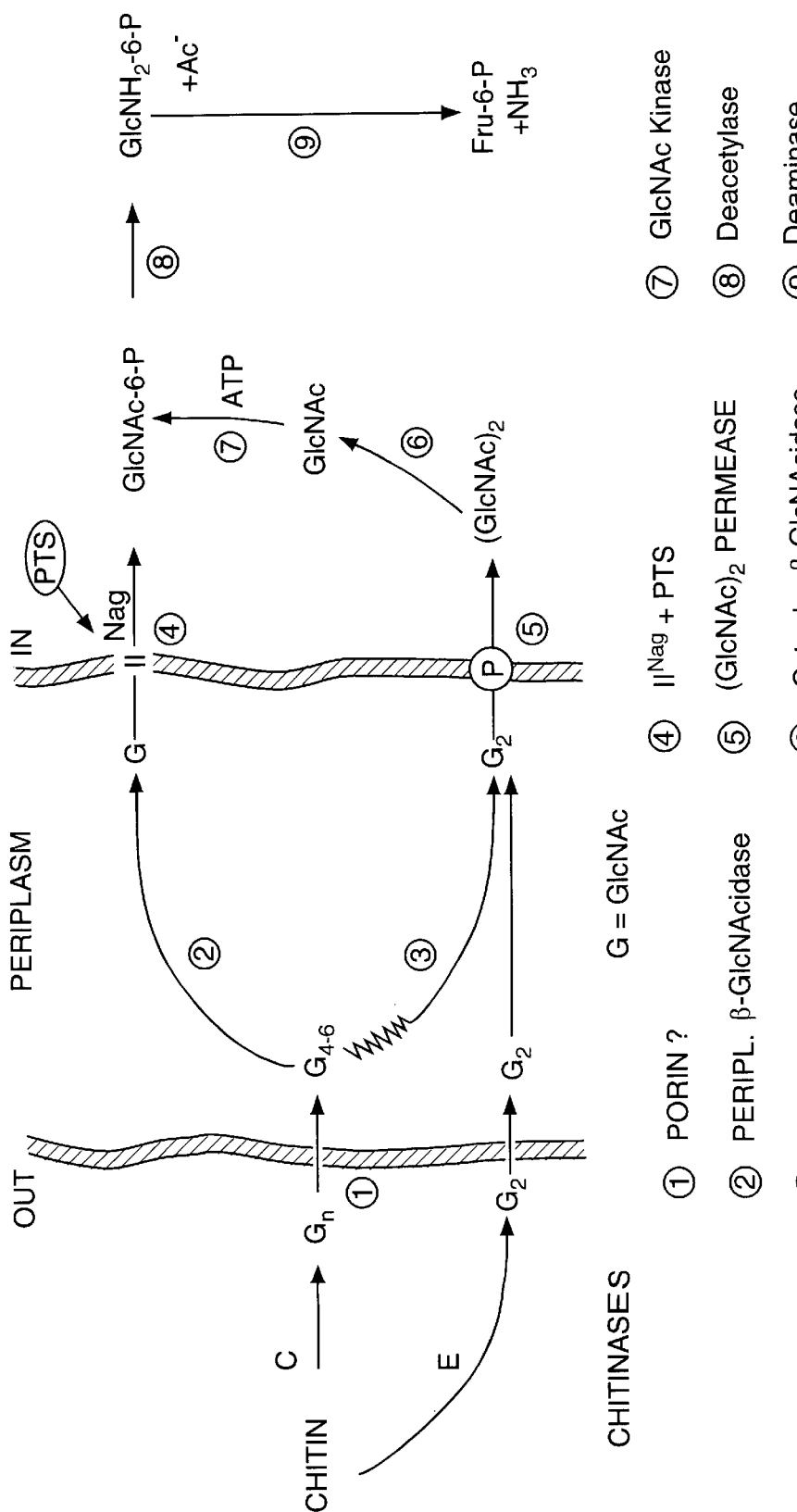
FIG. 1 is a schematic diagram of chitin degradation by *V. furnissii*. The enzyme Exo-II is not shown, but is presumed to split the linkage between the chitin-O-Tyr-protein and/or the chitin-O-polyphenols in invertebrate cuticles.

The functions of these enzymes in the chitin catabolic pathway are schematically illustrated in FIG. 1. An endoenzyme is defined as an enzyme that cleaves internal bonds in its macromolecular substrate. In the case of glycosidases that hydrolyze glycosidic bonds in polysaccharides, an "endoenzyme" hydrolyzes internal glycosidic bonds. A chitinase is an example of an endoenzyme. An "exoenzyme" is defined as an enzyme that progressively hydrolyzes the terminal units of macromolecular substrates. In the case of glycosidases, the exo-glycosidases are exoenzymes that hydrolyze the terminal (non-reducing) end of the polysaccharide chain.

The transformation of host cells with the cloned genes and the isolation and characterization of the recombinant enzymes are also detailed. The cloned genes are used to create four strains of *V. furnissii* having specific deletion mutations.

The enzymes, cloned genes and deletion mutants are used in a novel method for producing chitin oligosaccharides.

Chitin is the second most abundant organic substance in nature and is a homopolymer of β,1→4 N-acetylglucosamine residues. Approximately $10^{11}$ metric tons are produced annually in the aquatic biosphere alone. These huge quantities of highly insoluble polysaccharide represent a potential devastating threat to the environment. The oceans would be depleted of carbon and nitrogen in a matter of decades and the respective cycles would cease if chitin was not converted to a biologically useful form. In fact, marine sediments contain only traces of chitin. It is degraded primarily by chitinivorous bacteria, which are ubiquitous in the aquatic biosphere, and include species that grow at 0–4° C. Vibrios are the most common, widely distributed marine bacteria, and since many Vibrios are chitinivorous, the pathways and mechanisms by which they utilize chitin are of special interest.

Chitin degradation by *V. furnissii* involves several signal transducing systems, a multitude of proteins including extracellular and cytoplasmic enzymes, membrane transporters, chemoreceptors, an adhesion/deadhesion apparatus (including a lectin) that acts as a nutrient sensor, and possibly periplasmic solute binding proteins and specific porins. The genetic regulation of chitin catabolism involves a cascade, where chitin is the first and N-acetylglucosamine (GlcNAc) the final inducer. The complete pathway results in the conversion of chitin to fructose-6-P, acetate, and ammonia. However, the individual steps of the catabolic pathway remain to be elucidated. Part of the pathway is shown in FIG. 1.

The present invention includes substantially purified Endo-I, Exo-I, and Exo-II polypeptide or enzymatic fragments thereof. The term "substantially pure" as used herein refers to the enzyme which is substantially free of other proteins, lipids, carbohydrates or other materials with which it is naturally associated. One skilled in the art can purify the enzyme using standard techniques for protein purification. The substantially pure polypeptide will yield a single major band on a non-reducing polyacrylamide gel. The purity of the enzyme can also be determined by amino-terminal amino acid sequence analysis.

The invention includes a functional enzymatic polypeptide and functional enzymatic fragments thereof. As used herein, the term "functional polypeptide" refers to a polypeptide which possesses a biological function or activity which is identified through a defined functional assay and which is associated with a particular biologic, morphologic, or phenotypic alteration in the cell. Functional fragments of the the enzyme, or "enzymatic fragments", includes fragments of the enzyme as long as the activity, e.g., capable of hydrolyzing soluble chitin, of the enzyme remains. Smaller peptides containing the biological activity of the enzyme described herein are included in the invention. The biological function, for example, can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Minor modifications of the the enzyme primary amino acid sequence may result in proteins which have substantially equivalent activity as compared to the native enzyme described herein. Such modifications may be deliberate, as by site-directed mutagenesis, or may be spontaneous. All of the polypeptides produced by these modifications are included herein as long as the enzymatic activity of the native enzyme is present. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for the enzyme activity.

The enzyme polypeptide of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides an isolated polynucleotide sequence encoding a polypeptide having the amino acid sequence of SEQ ID NO:2, 4, or 6. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode The enzyme. It is understood that all polynucleotides encoding all or a portion of the enzyme are also included herein, as long as they encode a polypeptide with the enzyme activity (e.g., Endo-I, Exo-I, and Exo-II). Such polynucleotides include naturally occurring, synthetic, and intentionally manipulated polynucleotides. For example, portions of the mRNA sequence may be altered due to alternate RNA splicing patterns or the use of alternate promoters for RNA transcription. As another example, the enzyme encoding polynucleotide may be subjected to site-directed mutagenesis. The polynucleotide sequence for the enzyme also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of The enzyme polypeptide encoded by the nucleotide sequence is functionally unchanged. In addition, the invention also includes a polynucleotide encoding a polypeptide having an amino acid sequence of SEQ ID NO:2, 4, and 6 and having at least one epitope for an antibody immunoreactive with the enzyme polypeptide.

The polynucleotide encoding the enzyme of the invention includes the nucleotide sequence in SEQ ID NO:1, SEQ ID NO:3 and SEQ ID NO:5, as well as nucleic acid sequences complementary to those sequences. A complementary sequence may include an antisense nucleotide. When the sequence is RNA, the deoxyribonucleotides A, G, C, and T are replaced by ribo-nucleotides A, G, C, and U, respectively. Also included in the invention are fragments (portions) of the above-described nucleic acid sequences that are at least 15 bases in length, which is sufficient to permit the fragment to selectively hybridize to DNA that encodes the protein of SEQ ID NO: 2, 4 or 6. "Selective hybridization" as used herein refers to hybridization under moderately stringent physiological conditions (eg., temperature, salt conditions) and does not require complete complementarity. Nucleic acid sequences having 70–95% complementarity are preferred, and sequences having 90–90% complementarity are most preferred for selective hybridization.

DNA sequences of the invention can be obtained by several methods. For example, the DNA can be isolated using hybridization or computer-based techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; and 4) computer searches of sequnce databases for similar sequences.

Preferably the enzyme encoding polynucleotide of the invention is derived from a bacterial organism, and most preferably from Vibrionacese. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

The development of specific DNA sequences encoding and enzyme of the invention can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell to form cDNA.

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for enzyme peptides having at least one epitope, using antibodies specific for the enzyme. Such antibodies can be either polyclonally or monoclonally derived and used to detect expression product indicative of the presence of enzyme cDNA.

DNA sequences encoding an enzyme of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the enzyme encoding polynucleotide sequences may be inserted into a recombinant expression vector. The term "recombinant expression vector" refers to a plasmid, virus or other vehicle known in the art that has been manipulated by insertion or incorporation of the enzyme genetic sequences. Such expression vectors contain a promoter sequence which facilitates the efficient transcription of the inserted genetic sequence of the host.

The expression vector typically contains an origin of replication, a promoters as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding the enzyme can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Methods which are well known to those skilled in the art can be used to construct expression vectors containing the the enzyme coding sequence and appropriate transcriptional/ translational control signals. These methods include in vitro recombinant DNA techniques, synthetic techniques, and in vivo recombination/genetic techniques. (See, for example, the techniques described in Maniatis et al., 1989 Molecular Cloning A Laboratory Manual, Cold Spring Harbor Laboratory, N.Y.)

In bacterial systems a number of expression vectors may be advantageously selected depending upon the use intended for the expressed protein. For example, when large quantities of the enzyme are to be produced, vectors which direct the expression of high levels of fusion protein products that are readily purified may be desirable. Those which are engineered to contain a cleavage site to aid in recovering are preferred. Such vectors include but are not limited to the *E. coli* expression vector pUR278 (Ruther et al., *EMBO J.* 2:1791, 1983), in which the the enzyme coding sequence may be ligated into the vector in frame with the lac Z coding region so that a hybrid -lac Z protein is produced; pIN vectors (Inouye & Inouye, 1985, Nucleic acids Res. 13:3101–3109; Van Heeke & Schuster, 1989, J. Biol. Chem. 264:5503–5509); and the like. The Examples provide preferred host cells and vectors of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

Isolation and purification of microbial expressed polypeptide, or fragments thereof, provided by the invention, may be carried out by conventional means including preparative chromatography and immunological separations involving monoclonal or polyclonal antibodies.

Identification of the enzymes of the invention allows a novel method for the production of chitin oligosaccharides. The process preferreably uses intact cells, both wild type and mutants, to resolve the mixtures of chitin oligosaccharides. Wild type *E. coli* can only utilize GlcNAc, whereas wild type *V. furnissii* can utilize $(GlcNAc)_n$, where n=1–4 without using special methods for induction. Higher oligomers such as $(GlcNAc)_5$, $(GlcNAc)_6$ and chitin are also consumed by *V. furnissii*, but only after special conditions of induction. Intact induced *V. furnissii* cells consume 0.32 μmole GlcNAc/mg protein/min at 25° C. (48), which is about the same as the maximum rate of glucose utilization by *E. coli* at 37° C. $(GlcNAc)_2$ and $(GlcNAc)_3$ are consumed at about the same rate (per GlcNAc equivalent) by *V. furnissii*. $(GlcNAc)_4$ is catabolized more slowly. $(GlcNAc)_5$ and $(GlcNAc)_6$ are not utilized unless the cells are selectively induced on swarm plates (48,50). The critical point is that *V. furnissii* catabolizes $(GlcNAc)_n$ without releasing any lower oligosaccharides, despite the fact that the first steps in their metabolism is hydrolysis in the periplasmic space. The two established pathways (mono- and disaccharide) of catabolism for the tetra-and trisaccharide are shown in FIG. 1.

The pathways for metabolizing $(GlcNAc)_5$, $(GlcNAc)_6$ and higher oligomers are not yet known. These compounds are excellent substrates for the periplasmic chitodextrinase and β-GlcNAc-idase, and are very rapidly hydrolyzed in toluene permeabilized cells. Therefore, the problem in their utilization by $(GlcNAc)_2$ induced cells is that they cannot diffuse through the holes or porins in the cell envelope, the first barrier to all solutes in Gram negative bacteria. In *E. coli*, the cell envelope is penetrated by non-specific holes or porins (Omp C, Omp F, Pho E) with size limits of about 500 daltons. The molecular weights of the oligomers are: $(GlcNAc)_2$, 424; $(GlcNAc)_3$, 628; $(GlcNAc)_4$, 831; $(GlcNAc)_5$, 1,034; $(GlcNAc)_6$, 1,237. A few specific *E. coli* porins are known, such as the LamB protein, which permits diffusion of maltodextrins up to the decamer. $(GlcNAc)_2$ induces an outer membrane protein in *V. furnissii*, which may be a specific porin, and we are now cloning this gene and protein. We also believe that higher oligomers may induce other porin(s). There is no information on the non-specific porins of *V. furnissii*. Furthermore, the shapes and hydrodynamic volumes of molecules are the critical parameters in the diffusion process. However, assume that 500 daltons is the cut-off size for solutes diffusing non-specifically through the cell envelope of *V. furnissii*, then null mutants of the inducible, specific porins would consume $(GlcNAc)_2$, but nothing larger (perhaps $(GlcNAc)_3$ at a slow rate). Similarly, if specific inducible porins that accommodate larger oligomers are deleted, only the lower oligomers would be consumed from a mixture of oligosaccharides. A critical point will be to determine the size limits of the porin presumably induced by $(GlcNAc)_5$ and $(GlcNAc)_6$. If it is similar to the Lam B protein, then mixtures of $(GlcNAc)_n$, n=1–7, would be catabolized, leaving only $(GlcNAc)_n$, n>7 in the extracellular medium.

The point to be emphasized is that porins and porin deletions or mutations in intact *V. furnissii* could serve as exquisite molecular sieves, with virtually no limit in the quantity of material that could be processed.

Two steps are required to make the oligosaccharides: (A) conversion of chitin to a mixture of soluble oligosaccharides, $(GlcNAc)_n$ and (B) resolution of the mixture to obtain single pure oligomers, or, defined mixtures, such as $(GlcNAc)_4$ and $(GlcNAc)5$, the oligomers that are most active in inducing plant nodules (after appropriate modification).

GENERAL METHODS

Buffers. The composition and pH (at room temperature, unless otherwise noted) of commonly used buffers in this study are listed below.

| Buffer | Composition |
| --- | --- |
| EP (electroporation buffer) | 10% glycerol |
| Transformation buffer | 50 mM $CaCl_2$, 10 mM Tris-Cl, pH 7.5 |
| TE | 10 mM Tris-Cl, 1 mM EDTA, pH 8.0 |
| TAE | 40 mM Tris-acetate, 1 mM EDTA, pH 8.0, diluted from 50 X stock |
| Improved TBE | 127 mM Tris, 235 mM boric acid, 2.52 mM EDTA, pH 8.3, dilute from 10 X stock |
| SSC | 0.064 M NaCl, 0.012 M Na citrate, pH 7.5 |
| SHM | Used for "stringent" hybridization. 25 mM Na phosphate, pH 7.5, 5 X SSC, 5% instant Carnation milk, 40% deionized formamide, 0.1 mg/ml sonicated salmon sperm DNA. |

Bacterial Culture Media. Reagents used to prepare bacterial media were purchased from Difco Labs (Detroit, Mich.). The formulations of the culture media used in this study are listed below.

| Medium | Composition (g/l) |
| --- | --- |
| Artificial Sea Water (ASW) | NaCl, 23.6; $Na_2SO_4$, 4; $NaHCO_3$, 0.2; KCl, 0.66; KBr, 0.96; $H_3BO_3$, 0.026; $MgCl_2.6H_2O$, 10.6; $SrCl_2.6H_2O$, 0.04; $CaCl_2$, 1.48; $K_2HPO_4$, 0.04; $NH_4Cl$, 2.0; |
| Hepes-50% ASW | Hepes buffer, 11.9 (50 mM) pH 7.5; in 50% ASW |
| Lactate-ASW | D,L-lactate, 5; in Hepes-50% ASW |
| LB | Bacto-tryptone, 10; yeast extract, 5; NaCl, 10 |
| LMB | Bacto-tryptone, 10; yeast extract, 5; NaCl, 20 |
| Marine Medium 2212 | Bacto-peptone, 5; yeast extract, 1.0; in Hepes-50% ASW |
| MacConkey | Bacto-Peptone, 17; Proteose Peptone, Agar 3; Bile Salts, 1.5; NaCl, 5; Neutral Red, 0.075; Crystal Violet, 0.5; Bacto Agar, 15 |
| M9 | $Na_2HPO_4$, 6; $KH_2PO_4$, 3; NaCl, 0.5; $NH_4Cl$, 1; $MgSO_4$, 0.24; $CaCl_2$, 0.015; carbon source, 2; Thiamine-HCl, 0.002; casamino acids, 2 |
| Medium A | $KH_2PO_4$, 4.5; $K_2HPO_4$, 10.5; $(NH_4)_2SO_4$, 1; $MgSO_4$, 0.12; carbon source, 2; Thiamine-HCl, 0.002 |

Antibiotics were used in the following concentrations: ampicillin, 15 μg/ml (30 μg/ml for agar plates) and tetracycline, 5 μg/ml (10 μg/ml for agar plates).

Bacterial strains. *V. furnissii* 7225 (available from the ATCC), a wild type strain which is also designated *V. furnissii* SR1519, was maintained at room temperature in a soft agar slab consisting of (g/l): yeast extract, 3; bactopeptone, 10; NaCl, 10; and agar, 5, in Hepes-buffered 50% ASW (see below). *E. coli* strains K-12, HB101, BL21 (DE3) and XL-Blue were stored as frozen cultures in LB. Typically, strains were grown overnight in rich broth (plus appropriate antibiotics for cells containing plasmids) with vigorous shaking. Fresh medium was inoculated with cells from the overnight culture at a 1:20 or 1:50 dilution, and this culture was grown to the desired density, usually mid-exponential ($OD_{590}$=0.3–0.4).

Preparation of Bacterial Genomic DNA. Genomic DNA was prepared from *V. furnissii* SR1519 by the following procedures (28). A single colony was transferred into 100 ml of LB and grown overnight at 37° C. The cells were collected by centrifugation, resuspended in 5 ml buffer (50 mM Tris-Cl pH 8, 50 mM EDTA) and frozen at −20° C. A fresh lysozyme solution (5 mg in 0.5 ml of 0.25M Tris-Cl pH 8) was added to the frozen cells, the mixture was thawed with gentle mixing at room temperature, and was then placed on ice for 45 min. One ml STEP solution (29) was added and the lysed cells were heated at 50° C. for 1 h; an equal volume of TE-saturated phenol was added and the layers were emulsified gently for 5 min. The aqueous and organic layers were then separated by centrifugation, and the aqueous layer was removed and re-extracted with TE-saturated phenol. The RNA and chromosomal DNA were precipitated from the aqueous phase by adding 0.1 volume of 3M NaOAc followed by 2 volumes of cold EtOH. This precipitate was spooled onto a Pasteur pipet, transferred to a clean tube and incubated overnight at 4° C. with 5 ml of buffered RNAse (50 mM Tris-Cl pH 7.5, 1 mM EDTA, 200 μg/ml RNAse A). The solution was extracted twice with an equal volume of $CHCl_3$. The DNA was reprecipitated from the aqueous phase by adding ¹⁄₁₀ volume of 3M NaOAc and 2 volumes of cold EtOH. The final product was suspended in TE buffer and the DNA concentration was determined as described in Plasmid Purification.

An alternate method for preparing genomic DNA was the CTAB procedure (30): In this procedure, the cells are lysed with SDS and proteinase K, and contaminants are selectively precipitated with cetyl trimethyl ammonium bromide (CTAB) in 0.5M NaCl; at this concentration of NaCl, nucleic acids are not precipitated. Residual impurities are removed by shaking with phenol, chloroform, isoamyl alcohol, and the DNA precipitated with isopropanol.

Plasmid Purification. Plasmids were prepared by the method of Pulleyblank et al. (31) or by the alkaline lysis method (30). Cells harboring the plasmid of interest were grown in LB or M9 medium containing the appropriate antibiotic. The cells were then harvested by centrifugation, and were resuspended in buffer (150 mM NaCl, 10 mM Tris-Cl pH 8) at 15 ml buffer per g wet weight of cells. The cells were lysed at room temperature by the addition of ⅔ volume of 40 mM EDTA pH 8 with 1% SDS and 1 mg/ml pronase, and the cell debris was removed by centrifugation at 150,000×g. The nucleic acids were precipitated from the supernatant fluid by the addition of ⅓ volume 40% PEG 3350 in 2M LiCl, 20 mM Tris-Cl pH 8, 2 mM EDTA. This nucleic acid pellet was homogenized in 2.5M LiCl, 10 mM Tris-Cl pH 8, 2 mM EDTA and cooled to −20° C. to precipitate RNA, which was removed by centrifugation at 250,000×g. Finally, plasmid DNA was precipitated from the supernate with 2.5 volumes of cold EtOH. The plasmid pellet was washed with 70% EtOH to remove residual salts and was dissolved in TE buffer. The nucleic acid concentration (and relative level of protein contamination) was determined by measuring the $A_{280}$ and $A_{260}$ of the preparation, where 1.0 $A_{260}$=50 μg DNA. For large scale plasmid preparations, cells were grown in 1 liter of medium, while for minipreps, cells were grown overnight in 10 ml of medium. Typically, 300–700 μg of plasmid was obtained using the large-scale protocol, and 5–10 μg from the miniprep protocol.

The alkaline lysis method is as follows: The cells are lysed in alkaline SDS, which denatures genomic and plasmid DNA. After neutralizing, the plasmid DNA is selectively renatured, and purified by treating with RNAase A, phenol/chloroform, chloroform/isoamyl alcohol, and precipitated with ethanol or PEG.

Bacterial Transformation. The heat shock procedure described in Maniatis et al. (29) was used. Host cells were grown to mid-exponential phase using an overnight culture started from a single colony. Plasmid DNA (5–50 ng in TE buffer) or DNA from a ligation mixture (10–100 ng in ligation buffer suggested by ligase manufacturer) was added (1–2 μl) to a cell suspension of 50–100 μl on ice. Occasionally, the DNA in ligation mixtures was precipitated by adding 1/10 volume of 3M sodium-acetate, pH 4.6, and 2 volumes of ice cold ethanol, followed by incubation of the samples at −70° C. for 20 min. The resultant pellet was washed once with an equal volume of 70% ethanol, dried and resuspended to 10–20 μl TE prior to use in transformation reactions. Cells with the DNA were heat shocked for 1 min at 42° C. or for 3–5 min at 37° C. in sterile glass tubes, 0.5–1.0 ml of LB was immediately added to the tubes and the cells were allowed to recover for 30–60 min at 37° C. with vigorous shaking. The transformed cells were then plated on selective media. Transformation efficiency was usually monitored by using a known amount of a control plasmid (pBR322).

An alternate transformation procedure involving electroporation was also used. The Cell-Porator® system from GIBCO-BRL and the manufacturer's recommended procedures were used (32). The Cell-Porator consists of a system for placing a suspension of cells and plasmids between two electrodes. Brief unidirectional electrical pulses render the cell membranes temporarily permeable to the DNA. Mid-exponential cells grown in LB were harvested and washed with EP and resuspended to 1/100 volume of the original culture in EP. These cells were either used immediately or frozen for later use. DNA (10–50 ng in 1–2 μl) was added to 30 μl of cells. The electroporation settings used were those recommended by the manufacturer (32). Efficiency was determined as described in the heat shock procedure.

Restriction Enzyme Digestion and Analysis of Plasmid Bacteriophage and Bacterial Genomic DNA. Standard procedures were followed (29,30) for restriction enzyme digestions and analysis of the fragments generated by these digestions. Generally, 0.5–1 μg of DNA, purified as described, was digested with 1–5 U of the desired restriction enzyme under the conditions suggested by the manufacturer. In situations where digestion by more than one enzyme was desired, the digests were usually performed separately; the DNA was precipitated (by the addition of 1/10 volume 2.5M NaOAc and 2.5 volumes of cold EtOH), dried, and the second digest was then performed. When double digestions were performed, the first enzyme used was the one requiring a lower concentration of salt; in this manner, inhibition of the second restriction enzyme (by salts remaining from the first digest) was minimized. The resulting DNA fragments, in BPB/Ficoll tracking dye, were separated by electrophoresis through 0.8% agarose gels in TAE buffer (29). Agarose gels were 13.4×14.2×0.5 cm submerged horizontal gels. The gels were run at 4–5 V per cm until the BPB dye was 2–3 cm from the bottom of the gel. DNA within the gel was visualized by soaking the gel in a 0.1 μg/ml solution of ethidium bromide for 20 min, followed by rinsing in H$_2$O for 10 min. The gel was photographed under UV illumination with a Polaroid Land Camera (Polaroid Type 667 film). A HindIII digest of λ DNA was used for molecular weight standards.

DNA fragments were eluted from Agarose gels using standard techniques including electroelution (30), purification using GeneClean®II (Bio 101, Inc., LaJolla, Calif.) (28), and the band intercept method (29). GeneCleanII comprises a silica matrix to which DNA in cell extracts is adsorbed under conditions of high ionic strength. The matrix is washed free of protein and other contaminants, and highly purified DNA is eluted at increased temperature, low ionic strength.

Ligations were performed using standard conditions (30). Blunt-end ligations were performed at 18° C. for 18 hr, whereas compatible overhanging ends were incubated with ligase for 2 hr at 25° C. Inserts in cloning experiments were purified from gels as described above and ligated to phosphatase-treated vector that had also been cut to produce compatible ends in a ratio of 2–5:1.

pBR322 was used as the vector for much of this work, but pUC18, pUC19, and pvex were also employed. pVex is a high copy number plasmid with a T7 polymerase promoter near its multiple cloning site, thus allowing for overexpression of the desired gene product. The polymerase is generated in the host cell E. coli BL21(DE3) by induction with IPTG. Thus, in experiments involving ligations of cloned DNA fragments into pVex, induction of expression by IPTG indicates that the cloned gene is in proper orientation with respect to the T7 polymerase promoter.

DNA Sequence Analysis. The DNA prepared from the recombinant clones was sequenced by the dideoxy method using a U.S. Biochemical Sequenase® sequencing kit (30, 31). The kit provides buffers, labeling mixtures, termination dideoxy nucleoside triphosphates, and T7 DNA polymerase. Plasmid preparations were used in double-stranded sequencing according to the manufacturer's recommended procedures.

The V. furnissii DNA insert containing the desired gene was subcloned into two single-strand producing phagemids, the pBluescript SK+ and SK− vectors (33). These phagemids contain the intergenic (IG) region of the filamentous f1 phage, which encodes the cis-acting functions required for packaging and replication. A pBluescript recombinant transformed into E. coli with the F' episome will extrude a single-stranded f1 packaged phage when the bacterium has been infected by a helper phage. The SK+ construct extrudes the single strand corresponding to the coding strand of a β-galactosidase gene contained in the vector, while the SK− produces the other strand. This approach enables one to sequence in both directions. Single-stranded templates were prepared from pSK+/− constructs containing the V. furnissii gene in the vector transformed into XL1-Blue cells (34). VCSM13 was used as the helper phage to produce the single strand (33). Single-strand DNA was purified from clarified culture supernatants by PEG precipitation and by phenol/chloroform extraction (33). The radioisotopic label used in the dideoxy reactions was either α-[$^{35}$S]-dATP or α-[$^{32}$P]-dATP. sequencing reactions were analyzed on 6–8% polyacrylamide gels run at constant power (60–70 watts) in Improved TBE buffer. Gels were fixed in 5% methanol/10% acetic acid for 20–40 min and dried for autoradiography, with exposure times of 1 to 4 days.

DNA hybridizations. DNA fragments were hybridized to one other, by the method of Southern (30), to ascertain whether they contained the same or different genes. The DNA fragments were cut from the respective plasmids with restriction enzymes and gel purified as described above. The samples were heated at 65° C. for 10 min, and 6 ng each loaded per lane of a 1% Agarose gel. Following electrophoresis, the gel was washed sequentially with 0.1M HCl (10 min), 0.5M NaOH+1.5M NaCl (2×15 min), and 0.5M Tris, pH 7.4+1.5M NaCl (2×15 min). A Southern transfer to nitrocellulose was performed overnight in 0.64M NaCl, 0.12M Na citrate, pH 7.5. The blot was allowed to dry and the original gel stained with ethidium bromide to determine whether all of the DNA had been transferred. The blots were then probed as follows. Labeled probes were prepared from the cloned genes by the random primer method (30), using a BMB Random Priming Kit® (Boehringer Mannheim Biochemicals, Indianapolis, Ind.) and α-[$^{32}$P]-dCTP. The kit contains standard DNA, hexanucleotide mixture containing all possible sequence combinations of hexanucleotides, deoxynucleoside triphosphates, and Klenow enzyme. One or more of the random hexanucleotides hybridize with the fragment to be labeled, and a strand complementary to the DNA is synthesized with labeled nucleotides (not provided in the kit) by extension of the hexanucleotide with the Klenow fragment of DNA polymerase I.

After purification (TCA precipitation, Sephadex columns), the specific activities of the probes were $10^8$–$10^9$ cpm per μg DNA. The probes (at least $10^6$ cpm aliquots each) were denatured, and hybridized to the membranes. Hybridization conditions varied from stringent to reduced stringency as follows (only the extremes are given): 65° C. overnight in 6× SSC buffer, 0.5% SDS, 5× Denhardt's solution (30), and 100 μg calf thymus DNA per ml; 37° C., 6× SSC, 10% dextran sulfate, 35% formamide. The blots were washed three times (10 min each) in 5× SSC, 0.1% SDS at 25° C., then for 60 min in 0.5 SSC, 0.1% SDS at 40° C. The blots were finally exposed to X-ray film.

SPECIFIC METHODS 1. endI gene encoding periplasmic chitodextrinase (Endo-I)

a. Cloning of endI gene encoding periplasmic chitodextrinase.

Figure 2:
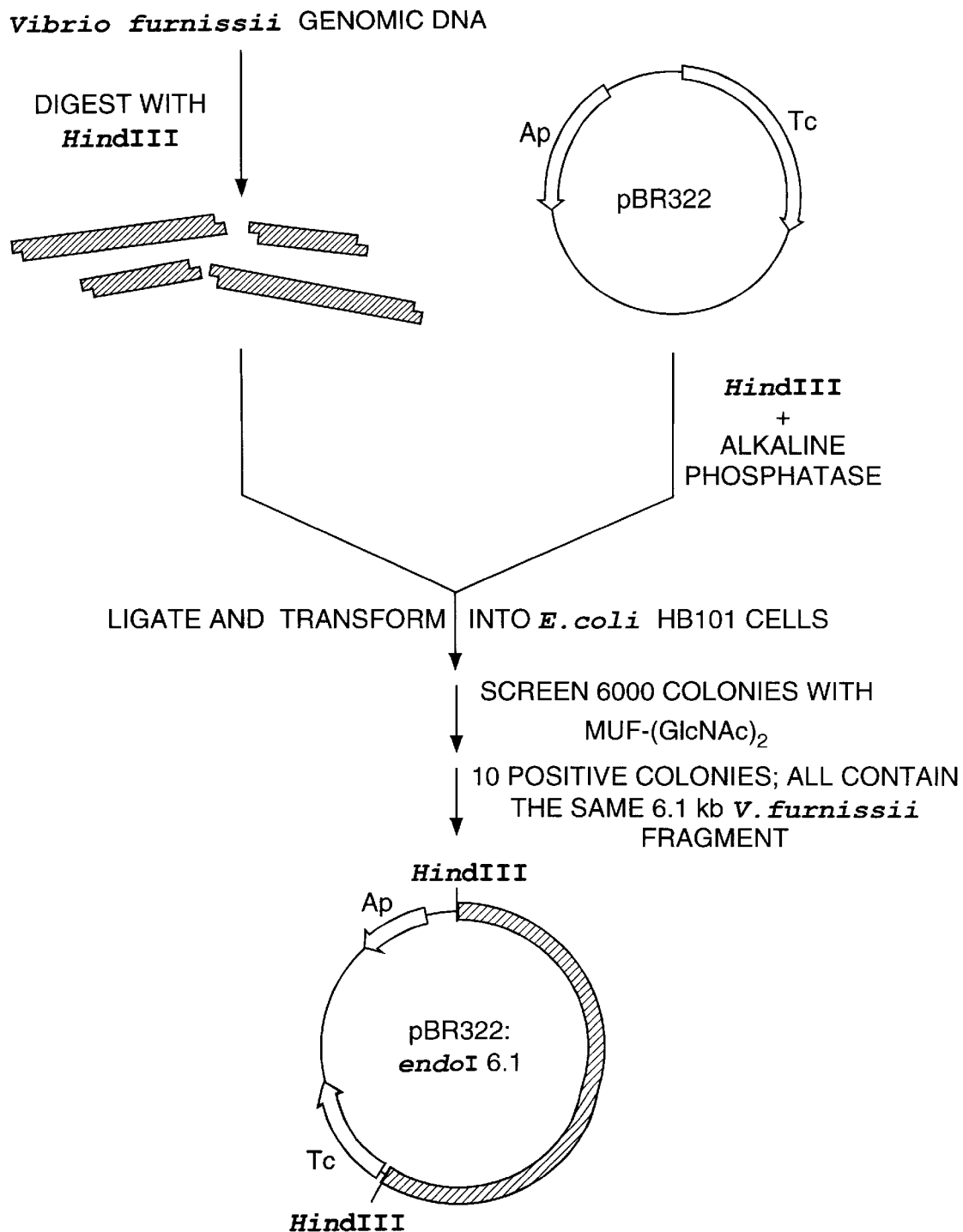
FIG. 2 summarizes the procedures used in the molecular cloning of the endI gene in *V. furnissii*.

Aliquots (6 μg) of *V. furnissii* genomic DNA were digested with HindIII, extracted with phenol and CHCl$_3$/isoamyl alcohol, and EtOH precipitated. pBR322 (2 μg aliquots) was similarly digested, and dephosphorylated with bacterial alkaline phosphatase (BRL, Inc.) according to the directions of the manufacturer. As shown in FIG. 2, the digested *V. furnissii* and plasmid DNA were ligated with T4 DNA ligase (BRL, Inc.), and the mixture used to transform *E. coli* as described above (heat shock). Several ratios of the DNA preparations were tested, and the maximum number of transformants was obtained with a ratio of 3:1, *V. furnissii* DNA: pBR322, and the highest frequency with *E. coli* HB101. After 60 min of growth at 37° C. in LBA (LB ampicillin medium), aliquots were plated to determine the number of recombinant plasmids; 68% of the Amp$^r$ cells contained recombinant plasmids (Amp$^r$ Tet$^s$).

The *E. coli* HB101 transformants were plated on LBA, individual colonies transferred to fresh plates containing a grid, grown overnight, and a replica of each grid was transferred to a sterile Whatman No. 1 filter paper. The papers were then sprayed with 9.5 mg 4-methyl-umbelliferyl-(GlcNAc)$_2$ per ml dimethyl formamide diluted 1:50 with 0.1M Tris, pH 7.4. (4-Methyl-umbelliferyl (MUF) glycosides are not fluorescent, whereas the product of hydrolysis, MUF, is highly fluorescent (35). After spraying, the papers were incubated at 37° C. for 15 min, sprayed again with saturated NaHCO$_3$ to enhance fluorescence, and immediately viewed under low wave length U.V. light. Transformants harboring endI were fluorescent; the colonies were picked from the original grids and single colony purified. Ten of 6,000 transformants gave positive results, and each contained an identical 6.1 Kb *V. furnissii* DNA fragment. The transformants were designated HB101:pBB22. The *V. furnissii* DNA fragment carried its own promoter as determined by cloning in both orientations in pUC vectors. The pBR322 vector carrying endI is designated pBR-EndoI.

b. Characterization of isolated endI gene

The isolated endI gene was sequenced by the SK+/− method described above and was found to comprise a sequence of 6180 base pairs. The entire nucleotide sequence is shown in SEQ ID NO:1. The *V. furnissii* DNA fragment contained one major open reading frame. The predicted amino acid sequence of the periplasmic chitodextrinase encoded by the endI gene is shown in SEQ ID NO:2 and consists of 1046 amino acids with a predicted molecular weight of 112.7 kDa. The predicted amino acid sequence contains a typical bacterial signal sequence for secretion into the periplasmic space (36). As described below, the protein is, in fact, processed by the *E. coli* host.

As indicated in the next section, the periplasmic chitodextrinase is an endoenzyme that cleaves soluble chitin oligosaccharides, but it is not a chitinase. Nevertheless, a search of the Swiss Protein Data Bank identified a region in the chitodextrinase, amino acid residues 300 to 700, which showed significant homology to a large number of chitinases from different sources. Eight amino acids were completely conserved in all of the homologous proteins, and in the chitodextrinase these are: Ser414, Gly416, Gly417, Phe456, Gly471, Asp473, Asp475, Asp561. Possibly, these conserved residues are at the active sites of the enzymes since they are all endo β-N-acetylglucosaminidases.

c. Characterization of recombinant periplasmic chitodextrinase

The recombinant periplasmic chitodextrinase has been purified to homogeneity from an *E. coli* transformant. The plasmid was used to transform *E. coli* BL21, grown in LBA medium, the cells extracted (French Press), nucleic acids precipitated with streptomycin, and the proteins fractionated with ammonium sulfate. The 70% fraction was chromatographed on a DEAE-sepharose column, followed by chromatography on hydroxylapatite, an ACA-34 gel filtration column, and finally on an HPLC-DEAE column. Activity was quantitated during purification by the rate of hydrolysis of p-nitrophenyl-(GlcNAc)$_2$, and the enzyme was purified 460-fold and obtained in 15% yield.

The apparent molecular weight of homogeneous Endo-I by SDS-PAGE is 120 kDa, which agrees well with the predicted mass from the nucleotide sequence, 113 kDa.

In *E. coli*, the enzyme is periplasmic. Furthermore, *E. coli* BL21 processes Endo-I by removing the first 30 amino acid residues (which are very similar to the N-terminal consensus signal sequence in *E. coli* proteins). The N-terminal amino acid sequence of the homogeneous enzyme is identical to the predicted protein sequence (from the DNA sequence), starting at residue 31 of the predicted sequence through residue 48.

The chitodextrinase is inactive with chitin, but hydrolyzes soluble (GlcNAc)$_n$. The enzyme does not liberate the GlcNAc residues that begin and terminate the oligosaccharide chain. Thus, the products of hydrolysis are (GlcNAc)$_2$ and (GlcNAc)$_3$, depending on the substrate. For example, (GlcNAc)$_4$ yields only (GlcNAc)$_2$, and (GlcNAc)$_5$ yields equimolar (GlcNAc)$_2$ and (GlcNAc)$_3$.

2. exoI gene encoding periplasmic β-GlcNAcidase a. Cloning of exoI gene encoding periplasmic β-GlcNAcidase The exoI gene was cloned into *E. coli* HB101 exactly as described above for endoI except that the screening reagent was MUF-GlcNAc instead of MUF-(GlcNAc)$_2$. Three of 6,000 *E. coli* transformants, designated HB101:pBB20, exhibited β-N-acetylglucosaminidase activity, and each contained an identical 12.5 Kb fragment of DNA that did not hybridize to the *V. furnissii* DNA fragment in the plasmid pBB22 carrying endoI.

Figure 3:
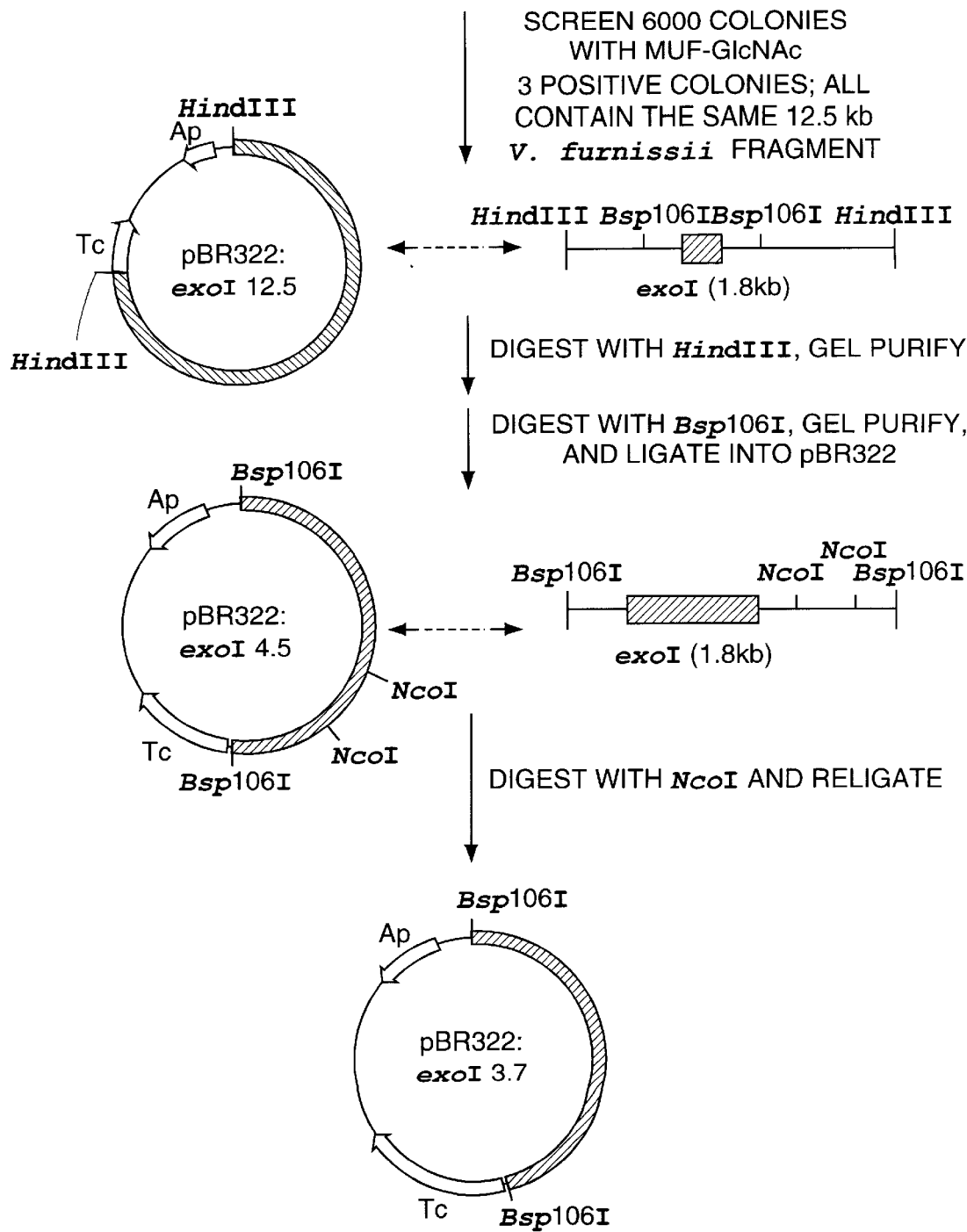
FIG. 3 summarizes the procedures used in the molecular cloning of the exoI gene in *V. furnissii*.

The β-GlcNAcidase gene in pBB20 was subcloned in two steps as shown in FIG. 3. The *V. furnissii* 12.5 Kb DNA fragment in pBB20 was treated with ClaI, yielding a 4.5 Kb fragment carrying exoI, which was ligated into two vectors, pBR322 and pVex, giving the constructs: pBR322:exoI4.5 and pVex:exoI4.5, respectively. The ClaI fragment was cloned into pVex in both orientations. However, only one showed a large increase in β-GlcNAcidase activity when IPTG was added to induce the T7 polymerase in *E. coli* BL21(DE3), and this clone was used for all subsequent work.

The 4.5 Kb DNA fragment contains two NcoI sites downstream from exoI. The plasmids pBR322:exoI4.5 and pVex:exoI4.5 were therefore treated with NcoI to remove 0.8 Kb of DNA, and the residual plasmids ligated to give pBR322:exoI3.7 and pVex:exoI3.7. Each plasmid carried the intact exoI gene. The 3669 bp fragment was completely sequenced.

b. Characterization of isolated exoI gene

The isolated DNA fragment containing the exoI gene in pVex:exoI3.7 was sequenced by the double stranded method, and comprises a nucleotide sequence of 3670 base pairs. The entire nucleotide sequence is shown in SEQ ID NO:3.

The open reading frame in pVex:exoI3.7 begins at nucleotide 844. There is a stop codon at 2676, putative -10 and -35 promoter regions, and a ribosome binding site. The predicted amino acid sequence of the periplasmic β-GlcNAcidase encoded by the exoI gene is shown in SEQ ID NO:4 and consists of 611 amino acids having a predicted molecular weight of 69.4 kDa.

A search of the Swiss Protein Data Bank showed 6 proteins with significant homologies to the translated open reading frame of exoI. The proteins are all hexosaminidases, including the α and β chains of human hexosaminidase. In general, the homologies were restricted to a domain in the *V. furnissii* enzyme spanning residue 200–400, and comprised about 30% identity in about a 200 amino acid overlap in the other hexosaminidases. It is important to emphasize that enzymes such as the human hexosaminidase differ considerably from the *V. furnissii* Exo-I in substrate specificity and pH optimum.

c. Characterization of recombinant periplasmic β-GlcNAcidase

In BL21(DE3):pVex:exoI3.7, the β-GlcNAcidase represents about 2.5% of the total protein in maximally induced cells (with IPTG). Exo-I was purified as described for Endo-I, omitting the hydroxylapatite step, and was obtained in homogeneous form after 40-fold purification and in 22% yield. Purification was followed by measuring the rate of p-nitrophenyl β-GlcNAc hydrolysis (PNP-GlcNAc).

The homogeneous enzyme exhibits an apparent mol. wt. of 68 kDa on SDS gels (compared to the predicted 69.4 kDA from the DNA sequence). The N-terminal 20 amino acid sequence of the homogeneous enzyme coincided exactly with the predicted sequence. Unlike Endo-I, which is a periplasmic enzyme in both *V. furnissii* and the *E. coli* transformants, Exo-I is periplasmic in the former, but not the latter. It appears that *E. coli* does not recognize the signal encoded in Exo-I.

The purified enzyme hydrolyzed aromatic glycosides of β-GlcNAc, such as PNP- and UMF-β-GlcNAc, and showed considerably lower activity on the corresponding N-acetylgalactosamine derivatives. The most active substrates were $(GlcNAc)_n$, n=3–6, and these compounds were hydrolyzed at pH optima 7–7.5. Most interestingly, at the pH of sea water, about 7.5, the enzyme showed only 2% of the activity with $(GlcNAc)_2$ compared to the other oligosaccharides. Thus, this enzyme is not a chitobiase, but it actively degrades the higher oligomers to GlcNAc and $(GlcNAc)_2$.

3. exoII gene encoding enzyme specific for aryl β-N-acetylglucosaminides a. Cloning of exoII gene encoding enzyme specific for aryl β-N-acetylglucosaminides

*V. furnissii* genomic DNA was digested with ClaI, the fragments ligated into pBR322, and the plasmids used to transform *E. coli* HB101 as described above. The transformants were screened with MUF-β-GlcNAc, exactly as described for screening the HindIII bank for the exoI gene.

Figure 4:
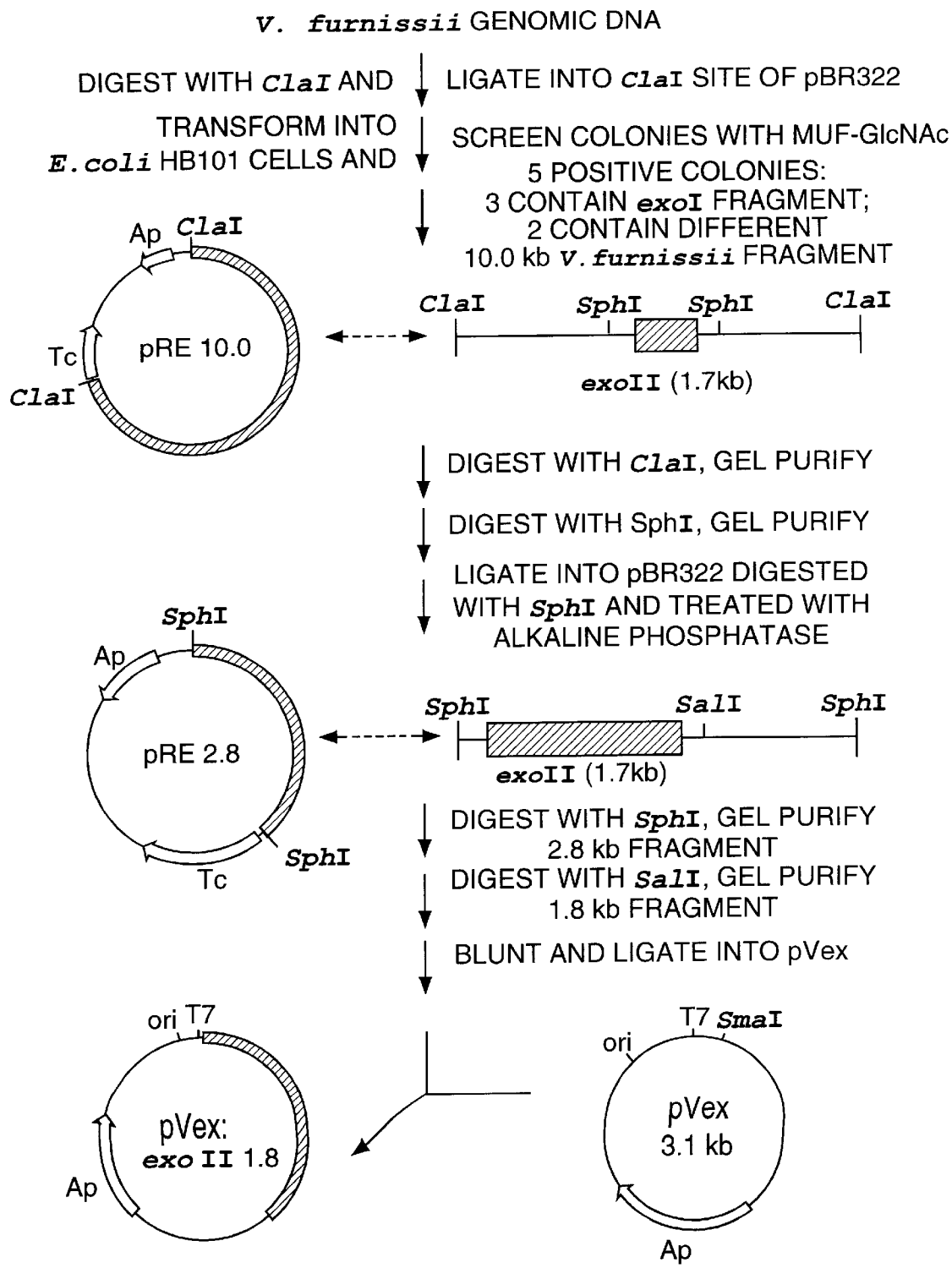
FIG. 4 summarizes the procedures used in the molecular cloning of the exoII gene in *V. furnissii*.

Five positive clones of 6,000 transformants were isolated and analyzed by Southern hybridization. Three clones contained exoI but two were different, and identical to one another. The two clones contained a 10.0 Kb *V. furnissii* DNA fragment (FIG. 4).

The plasmid (designated pRE100) was isolated, digested with SphI, yielding a 2.8 Kb fragment which was ligated into pBR322 and contained the exoII gene; the plasmid was designated pRE28. Finally, pRE28 was isolated, and the *V. furnissii* 2.8 Kb fragment digested with SalI, giving two fragments, 1.8 and 1 Kb respectively.

The 1.8 Kb SphI/SalI fragment was blunt ended, and ligated in both orientations into the SmaI site of pVex. Both orientations expressed Exo-II, indicating that the 1.8 Kb *V. furnissii* DNA fragment carries its own promoter; the plasmids are designated pVex:exoII1.8.

b. Characterization of isolated exoII gene

The isolated 1.7 Kb DNA fragment carrying the exoII gene was subcloned into pBluescript SK+/− and sequenced by the dideoxy method from single and double stranded DNA as described in "General Methods". The fragment comprised a sequence of 1713 base pairs, and the entire nucleotide sequence is shown in SEQ ID NO:5.

The 1713 base pair DNA fragment contained a single open reading frame of 984 base pairs. The start codon (residue 202) is preceded by a potential ribosomal binding site at residue 191, and -10 and -35 regions (residues 184 and 166, respectively). A potential rho independent termination signal, a region with diad symmetry (22 bp) was found following the translational termination signal.

c. Characterization of recombinant enzyme specific for aryl β-N-acetylglucosaminides The predicted amino acid sequence of the enzyme specific for aryl β-N-acetylglucosaminides encoded by the exoII gene is shown in SEQ ID NO:6 and consists of 328 amino acids having a predicted molecular weight of 36 kDa. The translational start site was confirmed by sequencing 16 N-terminal amino acids from pure recombinant protein. No apparent N-terminal secretory signal sequence is present downstream from the start site.

A computer search of protein sequences in the Swiss Prot-gene bank, showed that Exo-II is a unique β-GlcNAcidase, with no homology to other published β-GlcNAcidase sequences. However, the search revealed significant similarity to five bacterial and yeast β-glucosidases. The highest degree of similarity was found to a β-glucosidase from *Agrobacterium tumefaciens* (37). The protein shares 26% identity in a stretch of 153 amino acids. This stretch of amino acids includes the catalytic site of the β-glucosidase (25 residues). Alignment of these 25 residues (the catalytic domain) from the two proteins, reveals 44% identity.

The enzyme was purified from transformants of *E. coli* BL21. Enzymatic activity was monitored continuously by following the rate of release of nitrophenol from the substrate PNP-β-GlcNAc. The enzyme was purified to homogeneity by precipitating nucleic acids from the crude extracts with streptomycin, followed by a 0–60% ammonium sulfate precipitation of the activity, DEAE column chromatography, and finally by chromatography on Sephadex G100. The enzyme was purified 58-fold and was obtained in 83% yield.

The apparent molecular weight by SDS-PAGE was 36 kDa, which agreed with the predicted molecular weight from the gene sequence, and the N-terminal 16 amino acid sequence coincided with the predicted sequence.

The pH optimum of the enzyme is 7.0, and it catalyzes the hydrolysis of aryl (e.g., nitrophenyl) β-GlcNAc glycosides, but no other nitrophenyl glycosides tested except a slight activity on nitrophenyl β-N-acetylgalactosaminide. It was inactive with alkyl β-GlcNAc glycosides, and was completely inactive on chitin oligosaccharides. Interestingly, GlcNAc is a potent inhibitor of Exo-II.

4. chiA gene encoding extracellular chitinase
   a. Cloning of chiA gene encoding extracellular chitinase The chiA gene was cloned as follows. V. furnissii genomic DNA was digested overnight at 37° C. with NruI and the DNA fragments purified with GeneCleanII. The fragments were ligated into the vector pUC19, previously digested with SmaI followed by treatment with alkaline phosphatase and gel purified using GeneCleanII. The ligation mixture was purified with GeneCleanII, electroporated into E. coli JM109, and plated onto LB ampicillin plates (50 μg ampicillin/ml). The colonies were screened with a 3.0 Kb EcoRI/HindIII DNA fragment of the plasmid pJP2547 (22). The plasmid carries the chitinase gene from the marine bacterium Aeromonas hydrophila. Probes were prepared from the plasmid digests thrice purified with GeneCleanII, and labeled with a BMB Random Priming Kit according to the manufacturer's instructions: the mixtures contained 25–50 ng of digested plasmid DNA, and 50 μCi [$^{32}$P]-dATP and gave probes containing 2–5×10$^8$ dpm/μg DNA. Labelled probe was separated from unincorporated nucleotides by the spun column method (30), and were denatured in 0.5M KOH at room temperature for 10 min.

Colony hybridization was carried out essentially as described by Sambrook et al. (29). Colonies were plated onto 85 mm agar plates containing the appropriate antibiotic and grown overnight at 37° C. One nitrocellulose filter (Millipore HATF 085–50) was put onto each plate and marked with India ink. The filters were removed and successively saturated with each of the following solutions: 1) 3 min with 10% SDS, 2) 5 min with 0.5M NaOH/1.5M NaCl, 3) 5 min with 0.5M Tris pH 7.4/1.5M NaCl, and 4) 5 min with 2× SSC; the filters were allowed to dry between treatments. After the final saturation with 2× SSC, the filters were dried at room temperature for 2 hours. Following U.V. crosslinking, the filters were soaked in 2× SSC for 10 min; colony debris was then soft enough to be gently scraped from the filter, using a wet tissue. The nitrocellulose discs were then prehybridized (2 hr, 37° C.), hybridized, and washed under "Stringent" conditions using the SHM mixture described above.

Hybridization was carried out for 16–20 hours at 37° C. using the denatured, labeled probe. These "Stringent" filters were then washed free of non-hybridized probe by two washes in 1× SSC/0.1% SDS, followed by two washes in 0.5× SSC/0.1% SDS at room temperature, allowing 15 minutes per wash.

Following washing, the blots were exposed to X-ray film.

Colonies which appeared to contain the desired chiA gene were picked and transferred to agar plates containing colloidal chitin. Transformants that expressed the extracellular chitinase yielded clear zones around the colonies.

Six clones which cleared the colloidal chitin after 2 days were detected from the 6000 NruI clones screened. These chitin-clearing clones also gave a strong signal for hybridization to the Aeromonas chitinase probe when compared with V. furnissii, JM109, and JM109/pUC controls.

Plasmids were isolated from the six transformants and restriction mapped; all showed an identical 3.0 Kb DNA fragment inserted into the pUC19 MCS vector. This plasmid is hereafter designated pCR-A. To ascertain that the insert contained in pCR-A was actually derived from V. furnissii, two Southern hybridizations were performed using the 3.0 Kb EcoRI/HindIII fragment from pCR-A as a probe, under "Highly Stringent" conditions (which would allow hybridization of only identical sequences). "Highly Stringent" prehybridization/hybridization mix was identical to SHM except that it contained 50% deionized formamide. The insert from pCR-A hybridized strongly to 3.0 and 7.2 Kb bands in NruI- and BglII- digested V. furnissii genomic DNA, but did not hybridize to E. coli K12 genomic DNA digested with the same enzymes. Likewise, the pCR-A-derived fragment hybridized with itself, but not with plasmids pBluescript II KS+ or SK+, pUC19, pVex, or pJP2547 (from which the Aeromonas probe had been isolated).

b. Characterization of isolated chiA gene

The entire V. furnissii insert was required for the chitin clearing phenotype; the 3.0 Kb EcoRI/HindIII fragment from pCR-A was cloned into pBluescript II KS+ and KS−, and single strand sequenced. Reactions containing dITP were included to resolve compressions which were numerous: G+C content was 63%.

The V. furnissii DNA fragment comprises a sequence of 2951 base pairs. The entire nucleotide sequence is shown in SEQ ID NO:7. The insert contains a single long open reading frame of 2598 base pairs, which would encode a gene product of 866 amino acids with a predicted molecular weight of 91.2 kDa. The predicted amino acid sequence for the extracellular chitinase encoded by the chiA gene is shown in SEQ ID NO:8.

Several regulatory regions were found in the 76 bases located 5' to the start site, including potential promoter regions (-10, -35). A predicted ribosomal binding site was found at bases 131–137. This sequence differs from the consensus (Shine and Dalgarno) by a single base substitution (AGGAAGT versus AGGAGGT). No cAMP/CPR binding site was detected in the insert, using a weighted matrix subsequence searching function of PC Gene (consensus sequence derived from data presented in de Crombrugghe et al. (38) and Ebright et al. (39)). In the sequence situated 3' to the coding region is a region with 2-fold rotational symmetry centered at base 2774 with a predicted free energy for stem-and-loop formation of $\Delta G° = -27.2$ kcal/mol. This structure resembles other prokaryotic rho-independent RNA polymerase termination signals (Rosenberg and Court, Holmes et al., (40) (41), Von Hippel et al., (42); transcription typically terminated 16–24 bases downstream from the center of the stem-loop structure (bases 2790–2798).

The chitinase gene was predicted to encode a pre-protein possessing a typical N-terminal signal sequence of 23–24 amino acids. This N-terminal sequence possesses the essential features of a standard signal peptide of the General Secretory Pathway: a short (6 amino acid) hydrophilic domain containing at least one K, a hydrophobic α-helical region rich in A and L, and a less hydrophobic C-terminal domain which terminates in ala-X-ala (36).

A search was conducted in the GenEMBL, GenBank and Swiss Prot databases for other genes and proteins having homologous nucleic acid and amino acid sequences. A high degree of homology was found between the cloned V.

furnissii chitinase and chitinase A of *Serratia marcescens* (Koo et al., 1992, SwissProt #P07254). Of the entire *S. marcescens* chitinase A, 71.4% of the amino acids were identical to those in the *V. furnissii* chitinase; an additional 20% of the amino acids were conserved between the two; since the molecular weight of *S. marcescens* chitinase A is 59 kDa, homology between the two proteins extends only through the N-terminal two-thirds of the *V. furnissii* chitinase. A multiple alignment was performed with other homologous proteins and the *V. furnissii* chitinase. There is a high degree of conservation among these proteins over a 140 amino acid stretch between L256 and F396 of the *V. furnissii* chitinase. This region is hypothesized to contain the chitinase active site (Kuranda and Robbins (9); Watanabe et al., (18); this region of homology also encompasses two residues essential for chitinase activity (Watanabe et al., (18)). No significant homology was found between *V. furnissii* chitinase and plant or fungal chitinases, chitinase D of *Bacillus circulans*, or hexosaminidases.

Some homology was found between *V. furnissii* chitinase and *V. furnissii* periplasmic chitodextrinase (Endo-I). Although 26 gaps were introduced in order to align the sequences, the same two regions of homology noted by Kuranda and Robbins (9) are present. Additionally, one of the two "essential" amino acids, D311, is conserved between the two proteins.

c. Characterization of recombinant extracellular chitinase

The cloned protein is expressed constitutively in *E. coli* BL21; only about 10% of the enzyme is secreted, which is not surprising since *E. coli* secretes very few extracellular proteins. The enzyme was purified to homogeneity as follows.

*E. coli* BL21 transformants harboring the plasmid pCR-A were grown to stationary phase, and ruptured in a French Pressure Cell. The supernatant fluid was treated with streptomycin sulfate to remove nucleic acids, the proteins precipitated with solid ammonium sulfate (to 85% of saturation), and the protein pellet extracted with decreasing concentrations of ammonium sulfate. Chitinase activity was found in the 20–40% fraction, and was applied to a C4-cellufine reverse phase column. The latter was eluted with a gradient of decreasing ammonium sulfate, and active fractions were combined, dialyzed against 50 mM pyridine acetate buffer, pH 6, and adsorbed to a DEAE-Sepharose CL-6B column equilibrated with the same buffer.

The column was washed, and eluted with a linear gradient of the buffer containing increasing concentrations of NaCl, the active fractions were pooled, purified by gel filtration on a Sepharose CL-6B column, and finally chromatographed on phenyl-Sepharose CL-4B (eluted with 50 mM Tris, pH 7.5). The enzyme was purified about 33-fold, and the yield was 64%. The method of assay was to measure the rate of release of soluble counts from [$^3$H]-acetyl labeled chitin (43).

The homogeneous protein is approximately 102 kDa (SDS-PAGE), which is somewhat higher than the molecular weight predicted from the DNA sequence (91.2 kDa). Gel filtration studies show that the protein exists as a monomer. The optimum conditions for chitin hydrolysis are pH 6.0, 37–42° C., and 50–100 mM NaCl.

N,N'-diacetylchitobiose, or (GlcNAc)$_2$, is produced from chitin, and no intermediates are detected at even the earliest time points (1 minute). After prolonged incubation of the chitin with the enzyme (1–3 days), significant quantities of GlcNAc were also detected.

5. Production of site directed deletion mutants in *V. furnissii*

The methods for the production and the characterization of each of the two specific deletion mutations in the endI or the exoI genes in *V. furnissii* are as follows.

The general procedure is to use a "suicide vector", i.e., one that cannot be replicated in *V. furnissii* because the vector lacks an origin of replication that is recognized by the host cell. In this approach, the vector contains a host gene or a fragment of the gene interrupted by an antibiotic marker. That is, the antibiotic cartridge is flanked on each side by DNA from the gene that is to be deleted. When the plasmid is transferred to *V. furnissii*, homologous recombination in each of the flanking regions results in insertion of the antibiotic cartridge into the host genome, giving a site directed null or deletion mutant.

The method of Simon et al. (44) involves conjugal transfer of plasmids from an *E. coli* mobilizing donor (IncP-type) to any Gram negative bacterium. The plasmid (e.g., a modified pACYC184) contains the Mob site for mobilization, and can only be propagated in the donor. From 5–10% of the transconjugants consisted of double crossovers, giving the desired dual recombinant null mutant.

The basic method has been improved, and used with two species of Vibrios (45–47). A vector, pNQ705 was constructed from pBR322 in which its origin of replication was deleted, and replaced with R6K Ori and therefore, pNQ705 can only be replicated in cells containing π, a protein encoded by the pir gene. An *E. coli* λ pir lysogen is used to amplify the plasmid. pNQ705 also carries the mobilizing genes required for conjugal transfer of the plasmid to another cell, Cm$^r$ and a multiple cloning site.

After amplification of the plasmid in an appropriate *E. coli* host strain, S17-1, it is transferred by conjugation into recipient cells where it cannot be replicated. Antibiotic resistant recipient cells are therefore recombinants. Miller and Mekalanos (46) used this procedure to construct site-directed mutants of *V. cholerae* toxR, and Milton et al. (47) to construct similar null mutants of a metalloprotease gene in *V. anguillarum*.

In the present application, the reported procedures were modified to construct the suicide vectors, pNQT:EndoI::Cm and pNQT:Exo-I::Cm. The constructs contained the following: (a) Ori R6K, an origin of replication that requires the π protein for replication; (b) the Mob RP4 genes that permit the plasmid to be transferred (mobilized) into any Gram negative recipient such as *V. furnissii*; (c) a Tc$^r$, or tetracycline resistance gene and (d) the fragment of DNA encoding endoI or exoI interrupted with the Cm or chloramphenicol resistance gene.

Two strains of *V. furnissii* were used as recipients of the conjugations, *V. furnissii* SR1519 (wild type) and *V. furnissii* AP801, a mutant in nagE (the GlcNAc permease) that has been described (48–50). A similar protocol was followed for constructing pNQT:ExoI::Cm and the corresponding null mutants. The deletion mutants were characterized by Southern blots, which showed that the Cm$^r$ cartridge had been inserted in the proper position in the *V. furnissii* genomic DNA.

a. Production and characterization of strain SR1545.15

Figure 5:
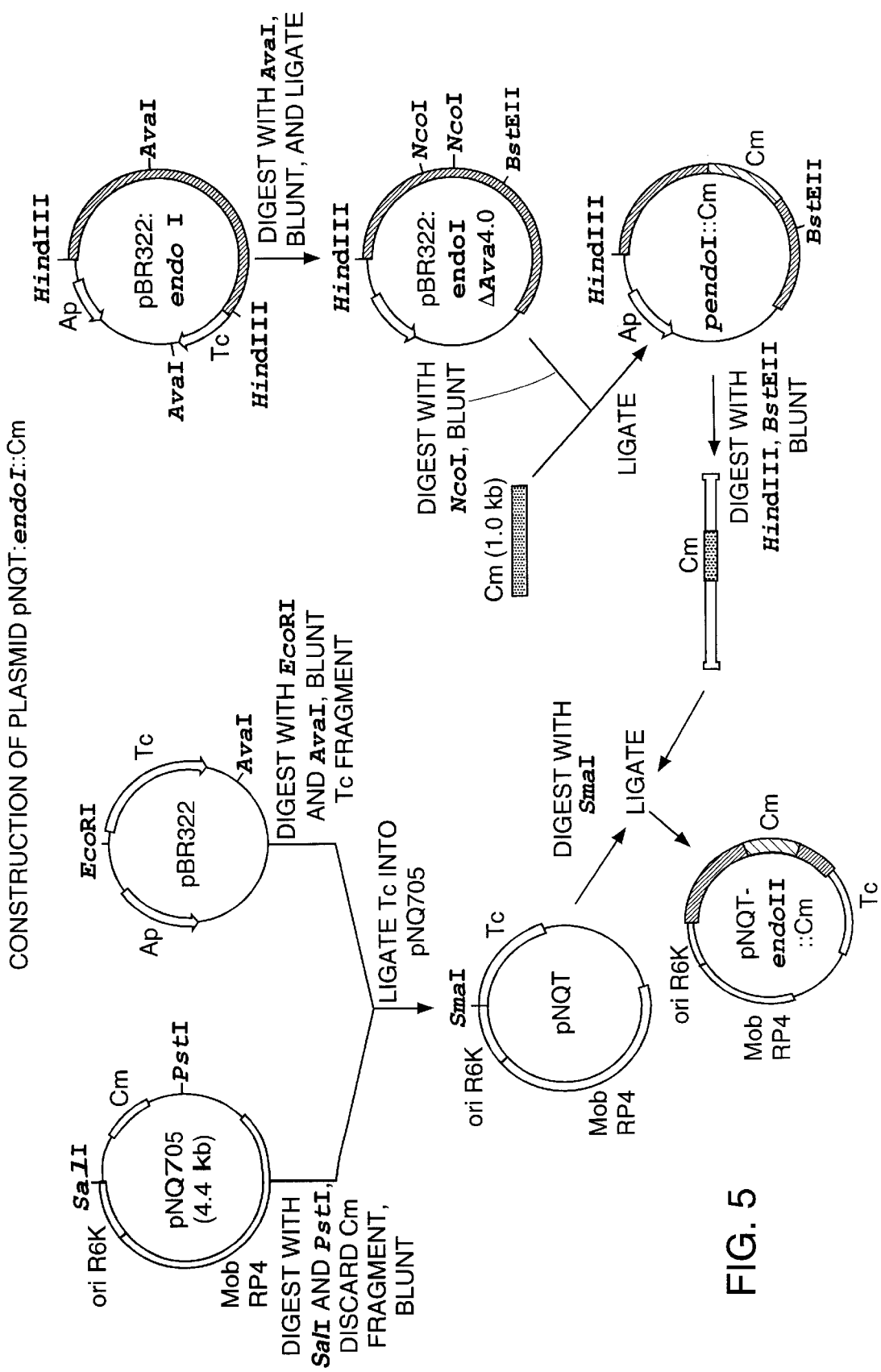
FIG. 5 outlines the procedure used to construct the plasmid pNQT:endI::Cm.
Figure 6:
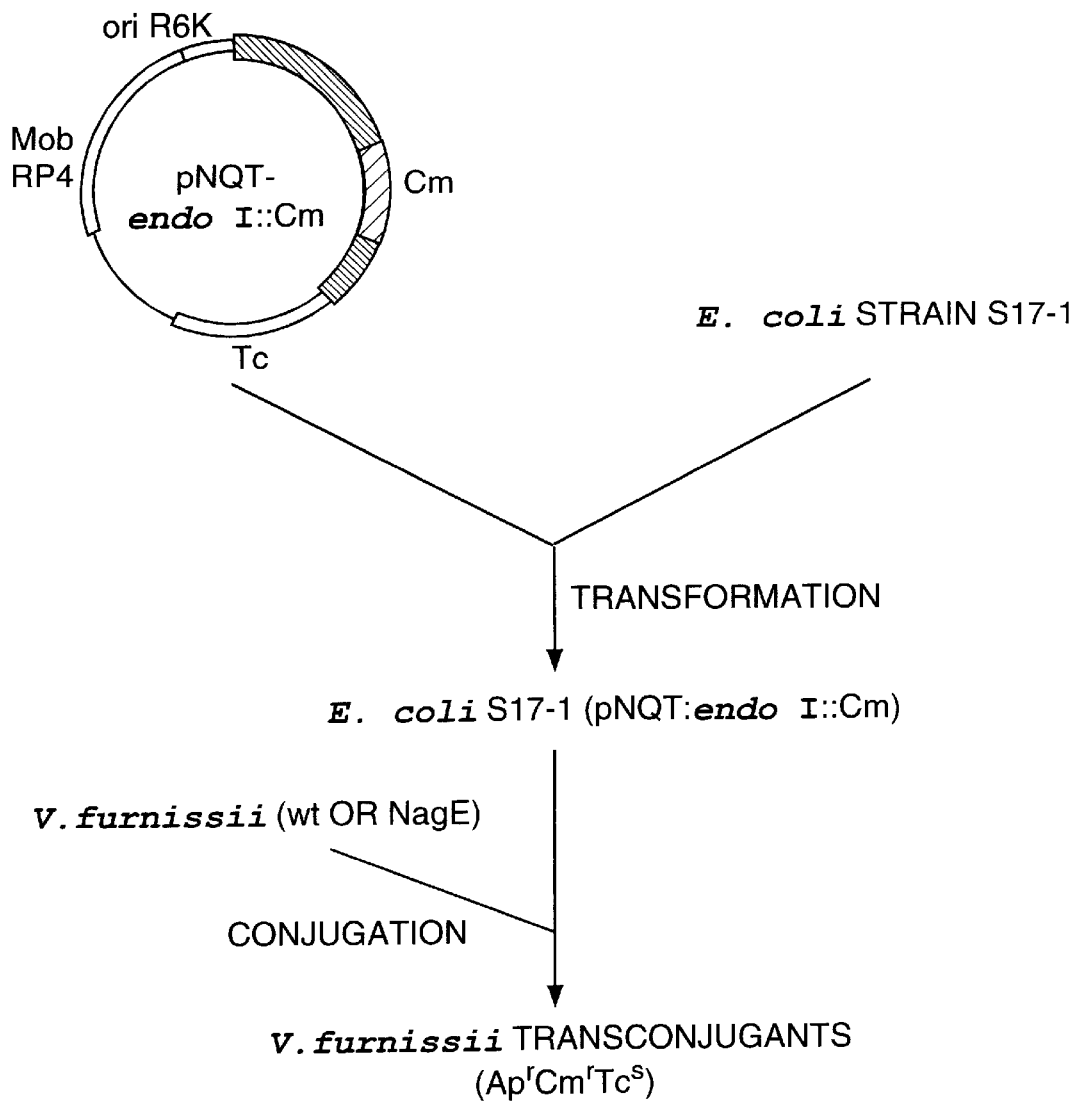
FIG. 6 outlines the procedure used to construct the *V. furnissii* endI deletion mutant.

The construction of pNQT-EndoI::Cm and of the *V. furnissii* null mutants is illustrated schematically in FIGS. 5 and 6.

*V. furnissii* strain SR1545.15, or SR1519[EndoI::Cm] was prepared as follows. The wild type *V. furnissii* SR1519 was conjugated with *E. coli* S17-1, which harbored the plasmid pNQT-EndoI::Cm. The transconjugants (several thousand) were Ap$_r$Cm$_r$Tc$_s$. After purification of several clones, the genomic DNA was shown to contain the Cm$^r$ insert in endoI by the methods described above.

*V. furnissii* strain SR1545.15 has a deletion between base pairs 1670 and 2236 in the endI gene, and the Cm$^r$ gene is inserted in this region. In other words, the endI open reading frame ends at bp 1669, followed by the inserted $Cm^r$, followed by the remainder of the ORF, starting with bp 2237.

b. Production of strain SR1540.11

Strain SR1540.11 was prepared exactly as described for strain SR1545.15, except that the deletion was constructed in *V. furnissii* AP801, i.e., SR1540.11 is AP801[EndoI::Cm]. It was characterized by the same methods used for SR1545.15. Strain SR1540.11 has precisely the same deletion as SR1545.15.

c. Production and characterization of strain SR1550.304

Figure 7:
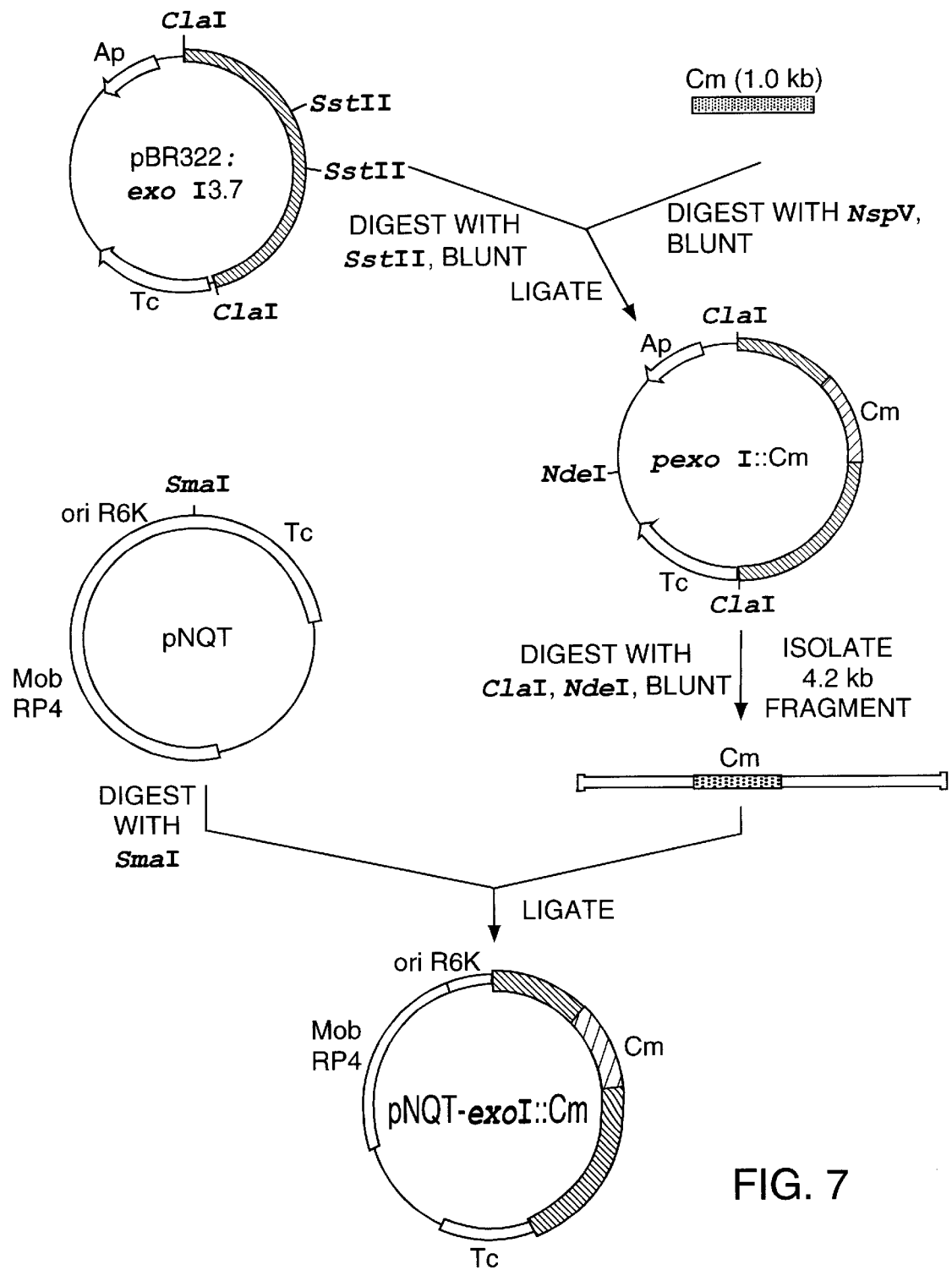
FIG. 7 outlines the procedure used to construct the plasmid pNQT:exoI::Cm.

Strain SR1550.304 was prepared as follows. The plasmid pBR322:exoI3.7 is described above, and contains the gene exoI, which expresses the enzyme Exo-I. The plasmid was treated with SstII, which cuts exoI at bp 1170 and 1634. After blunt ending the two ends, they are ligated to $Cm^r$, which has also been blunt ended (FIG. 7). Thus, there are about 1.17 Kb of exoI upstream of the 5' terminus of $Cm^r$, and 2.0 Kb of exoI at the 3' terminus. The interrupted gene is then cut from the plasmid with ClaI and NdeI, blunted, and ligated into the SmaI site of pNQT, giving pNQT:ExoI::Cm. The remaining steps are exactly as described for constructing strain SR1545.15, yielding the null (deletion) mutant *V. furnissii* SR1550.304, or, SR1519[ExoI::Cm]. The deletion mutant contains $Cm^r$ inserted into exoI, which has been deleted between bp 1170–1634.

d. Production and characterization of strain SR1550.104

Strain SR1550.104 was prepared precisely as described for SR1550.304 except that the deletion was transferred by homologous recombination into the host *V. furnissii* AP801. Strain SR1550.104 is *V. furnissii* AP801[ExoI::Cm].

Two steps are required to make the oligosaccharides: (A) conversion of chitin to a mixture of soluble oligosaccharides, $(GlcNAc)_n$ and (B) resolution of the mixture to obtain single pure oligomers, or, defined mixtures, such as $(GlcNAc)_4$ and $(GlcNAc)_5$, the oligomers that are most active in inducing plant nodules (after appropriate modification).

STEP A: Chitin→soluble $(GlcNAc)n$

Two methods give the desired products:

1. Partial acid hydrolysis of particulate chitin yields a mixture of soluble oligomers, some of which are partially deacetylated. The mixture is then quantitatively reacetylated with acetic anhydride in water (55,56).

2. A mixture of lower oligosaccharides, $(GlcNAc)_n$, n=2–4, and possibly some $(GlcNAc)_5$ are produced by the action of lysozyme on chitin (62). Egg white lysozyme is plentiful, commercially available, and quite inexpensive (about \$10/gram).

STEP B: Mixed $(GlcNAc)_n$→A single $(GlcNAc)_n$

Table I presents examples of procedures of the present invention that can be used to prepare chitin oligosaccharides. These methods result in obtaining large quantities of pure oligosaccharides by using appropriate recombinant enzymes and/or intact cells to resolve the mixtures.

TABLE I

METHODS FOR PREPARING CHITIN OLIGOSACCHARIDES

| DESIRED $(GlcNAc)_n$ | STARTING MATERIAL | STEPS | EXPECTED PRODUCTS |
|---|---|---|---|
| $(GlcNAc)_2$ | Chitin | 1. E-chitinase<br>2. *E. coli* | 1. $(GlcNAc)_2$ + (GlcNAc)<br>2. $(GlcNAc)_2$ |
| $(GlcNAc)_3$ | Soluble $(GlcNAc)_n$ | 1. Endo-I<br>2. *V. furnissii* Exo-I deletion, SR1519 | 1. $(GlcNAc)_3$ + $((GlcNAc)_2)$<br>2. $(GlcNAc)_3$ |
| $(GlcNAc)_4$ | Soluble $(GlcNAc)_n$ or chitin | 1. Exhaustive lysozyme<br>2. *V. furnissii* Endo-I deletion, SR1519 | 1. $(GlcNAc)_4$ + $((GlcNAc)_n,$ n = 1–3)<br>2. $(GlcNAc)_4$ |
| $(GlcNAc)_5$ | Soluble $(GlcNAc)_n$ or chitin | 1. Partial lysozyme<br>2. *V. furnissii* Endo-I deletion, SR1519 | 1. $(GlcNAc)_5$ + $((GlcNAc)_n,$ n = 1–4)<br>2. $(GlcNAc)_5$ |
| $(GlcNAc)_n$ n ≥ 5 | Soluble $(GlcNAc)_n$ | *V. furnissii* Endo-I deletion, SR1519 | $(GlcNAc)_n$ n ≥ 5 |

The normal substrate for egg white lysozyme is the N-acetylmuramyl glycosidic bond in bacterial cell walls, but it cleaves $(GlcNAc)_6$ at about 50% of this rate. The rates of cleavage of other $(GlcNAc)_n$ (relative to $(GlcNAc)_6$) are as follows: $(GlcNAc)_6$, 100; $(GlcNAc)_5$, 13; $(GlcNAc)_4$, 2.6; $(GlcNAc)_3$, 0.33; $(GlcNAc)_2$, 0.001.

The following Example describes the preparation of the disaccharide, $(GlcNAc)_2$, from chitin. Crude commercial chitin (40 g) was dissolved in concentrated HCl at 0° C., and reprecipitated by dilution in ice water. This step removes many impurities, and gives a finely divided, almost colloidal preparation of the chitin (63).

The E-chitinase preparation was the ammonium sulfate fraction from 10 g wet weight of *E. coli* BL21-chiA. The preparation in 50 mM pyridyl acetate buffer, pH 6, was dialyzed against the same buffer, mixed with the chitin preparation in the dialysis bag, and the mixture incubated for 3 days at 37° C. with stirring. Most of the precipitate was solubilized during the incubation. The dialysate was concentrated to remove the volatile buffer, yielding about 20 g of residue, consisting mostly of $(GlcNAc)_2$ and some GlcNAc. The mixture was treated as described above (for the preparation of ManNAc) with *E. coli* to remove the GlcNAc, yielding about 15 g of $(GlcNAc)_2$.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

Thus, it is to be understood that variations in the present invention can be made without departing from the novel aspects of this invention as defined in the claims.

The following references have been cited above and their entire disclosures are hereby incorporated by reference and relied upon:

1. Nalin, D., Cholera, Copepods, and Chitinase (1976) Lancet 2: 958.

2. Nalin, D. R., Daya, V., Reid, A., Levine, M. M., and Cisneros, L., Adsorption and growth of Vibrio cholerae on chitin (1979), Infection and Immunity 25: 768–770.

3. Lear, D. W. in Symposium on Marine Microbiology, Carl H. Oppenheimer, edit. (1963) C. C Thomas, publ., Springfield, Ill. P. 608.

4. Skjak-Braek, G., Anthonsen, T., and Sandford, P. (edit). Chitin and Chitosan. Sources, Chemistry, Biochemistry, Physical Properties, and Applic. (1988) Elsevier, New York, N.Y.

5. Flach, J., Pilet, P. E., Jolles, P., What's new in chitinase research? (1992) Experientia 48: 701–716.

6. Zechmeister, L, and Toth, G., Chromatographie der in der chitinreihe wirksamen Enzyme des emulsins. (1939) Enymologia 7: 165–169; Zechmeister, L, Toth, G., and Vajda, E., Chromatographie der in der chitinreihc wirksamen Enzyme der weinbergschnecke (helix pomatra). (1939) Enzyologia 7: 170–175.

7. Colowick S. P. and Kaplan N. O., Eds. Biomass, Part B, Lignin, Pectin, and Chitin. (1988) Meth.in Enzymol. 161: 403–524.

8. Joshi, S., Kozlowsld, M., Selvaraj, G., Iyer, V. N., and Davies, R. W., Cloning of the genes of the chitin utilization regulon of Serratia liquefaciens. (1988) J. Bacteriol. 170: 2984–2988.

9. Kuranda, K J., and Robbins, P. W., Cloning and heterologous expression of glycosidase genes from Saccharomyces cerevisiae. (1987) Proc Natl. Acad. Sci. USA 84: 2585–2589.

10. Robbins, P. W., Albright, C., and Benfield, B., Cloning and expression of a Streptomyces plicatus chitinase (chitinase-63) in *Escherichia coli*. (1988) J. BioL Chem. 263: 443–447.

11. Broglie, K E., Gaynor, J. J. and Broglie, R. M., Ethylene-regulated gene expression: molecular cloning of the genes encoding an endochitinase from *Phaseolus vulgaris*. (1986) Proc Natl. Acad. Sci. USA 83: 6820–6824.

12. Fuche, R. L, McPherson, S. A., and Drahos, D. J., Clontng of a Serratia marcescene gene encoding chitinase. (1986) Appl. Environ. Microbiol. 51: 504–509.

13. Horwitz, M., Reid, J., and Ogrydziak D., (1984) in Chitin, chitosan, and related enzymes. akikas, J. P. Ed. Academic Press Inc., New York. pp. 191–208.

14. Korneluk R. G., Mahuran, D. J., Neote, K., Klavins, M. H., O'Dowd, B. F., Tropak, M., Willard, H. F., Anderson, M-J., Lowden, J. A., and Gravel, R. A., Isolation of cDNA clones coding for the α-subunit of human β-hexosaminidase. Extensive homology between the α- and β-subunits and studies on Tay-Sachs disease. (1986) J. Biol. Chem. 261: 8407–8413.

15. Robbins, P. W., Trimble, R. B., Wirth, D. F., Hering, C., Maley, F., Maley, G. F., Das, R., Gibson, B. W., Royal, N., and Biemann, K., Primary structure of the Streptomyces enzyme endo-β-N-acetylglucosaminidase H. (1984) J. Biol. Chem. 259: 7577–7583.

16. Kamei, K., Yamamura, Y., Hara, S., and Ikenaka, T., Amino acid sequence of chitinase from *Streptomyces erythraeus* (1989). J. Biochem. 105: 979–985.

17. Kuranda, M J., and Robbins, P. W., Chitinase is required for cell separation during growth of *Saccharomyces cerevisiae*. (1991) J. Biol. Chem. 266: 19758–19767.

18. Watanabe, T., Suzuki, K., Oyanagi, W., Ohnishi K., and Tanaka, H., Gene cloning of chitinase A1 from *Bacillus circulans* WL-12 revealed its evolutionary relationship to Serratia chitinase and to the type III homology units of fibronectin. (1990) J. Biol. Chem. 265: 15659–15665.

19. Watanabe, T., Oyanagi W., Suzuki, K., Ohnishi, K., and Tanaka, H., Structure of the gene encoding chitinase D of *Bacillus circulans* WL-12 and possible homology of the enzyme of other prokaryotic chitinases and class III plant chitinases. (1992) J. Bacteriol. 174: 408–414.

20. Delic, I., Robbins, P., and Westpheling, J., Direct repeat sequences are implicated in the regulation of two Streptomyces chitinase promoters that are subject to carbon catabolite control. (1992) Proc. Natl. Acad. Sci. USA 89: 1885–1889.

21. Metraux, J. P., Burkhart, W., Moyer, M., Dincher, S., Middlesteadt, W., Williams, S., Payne, G., Carnes, M., and Ryals, J., Isolation of a complementary DNA encoding a chitinase with structural homology to a bifunctional lysozymc/chitinase. (1989) Proc. Natl. Acad. Sci. USA 86: 896–900.

22. Roffey, P. E., and Pemberton, J. M., Cloning and expression of an *Aeromonas hydrophila* chitinase gene in *Escherichia coli*. (1990) Current Microbiol. 21: 329–337.

23. Soto-Gil, R. W., and Zyskind, J. W., (1984) in Chitin, chitosan and related enzymes. Zakikas J. P. Ed. Academic Press Inc., New York. pp. 209–223; Jannatipour, M., Soto-Gil, R. W., Childers, L. C., and Zyskind, J. W., Translocation of Vibrio harveyi N,N'4iacetylchitobiase to the outer membrane of *Escherichia coli*. (1987) J. Bacteriol. 169: 3785–3791.

24. Soto-Gil, R. W., and Zyskind, J. W., N,N'-diacetylchitobiase of Vibrio harveyi. Primary structure, processing, and evolutionary relationships. (1989) J. Biol. Chem. 264: 14778–14783.

25. Wortman, A. T., Somerville, C. C, and Colwell, R. R., Chitinase determinants of *Vibrio vulnificus*: gene cloning and applications. (1986) Appl. and Environ. Microbiol. 52: 142–145.

26. Zhu, B. C. R., Lo, J., Li, Y., Li, S., Jaynes, J. M., Gildemeister, O. S., Laine, R. A., and Ou, C., Thermostable, salt tolerant, wide pH range novel chitobiase from *Vibrio parahaemolyticus*: isolation, characterization, molecular cloning, and expression. (1992) J. Biochem. 112: 163–167.

27. Laine, R. A., Expression and secretion of a cloned chitinase. (1991) 5th International Conf. on Chitin and Chitosan, Abstr. 20, Oct. 17–20, Princeton, N.J.

28. Anonymous 1993. Protocol in GeneClean II. Abstract.

29. Sambrook, J., E. F. Fritsch, and T. Maniatis. 1982. Molecular Cloning: a Laboratory Manual. 2nd ed. Abstract.

30. Sanger, F., S. Niklen, and A. R. Coulson. 1977. DNA sequencing with chain terminating inhibitors. *Proc. Natl. Acad. Sci., U. S. A.* 74:5463–5467.

31. Anonymous 1993. Protocols for DNA Sequencing with Sequenase (V2.0) T7 DNA Polymerase. 7th ed. Abstract.

32. Anonymous 1991. Cell-Porator Electroporation System I. Instructions Manual and Addendum: Experimental Data: Abstract.

33. Anonymous 1992. Recovery of single stranded DNA in Stratagene protocols: pBluescript II exo-mung DNA sequencing instruction manual. Abstract.

34. Bullosck, W. O., J. M. Fernandez, and J. M. Short. 1987. XL1-Blue: A high efficiency plasmid transforming recA *E. coli* strain with β-galactosidase selection. *BioTechniques* 5:376–379.

35. O'Brien, M. and R. R. Colwell. 1987. A rapid test for chitinase activity that uses 4-methylumbelliferyl N-acetyl-B-D-glucosaminide. *Appl. Environ. Microbiol.* 53:1718–1720.

36. Oliver, D. B. 1987. Periplasm and Protein Secretion. In *Escherichia coli* and *Salmonella typhimurium*: Cellular and Molecular biology. F. G. Neidhardt, editor. American Society for Microbiology, Washington, D.C. 56–69.

37. Castle, L. A., K. D. Smith, and R. O. Morris. 1992. *J. Bacteriol.* 174:1478–1486.

38. deCrombrugghe, B., S. Busby, and H. Buc. 1984. Cyclic AMP receptor protein: Role in transcription activation. *Science* 224:831–838.

39. Ebright, R. H., P. Cossart, B. Gicquel-Sanzey, and J. Beckwith. 1984. Mutations that alter the DNA sequence specificity of the catabolite gene activator protein of *E. coli*. Nature 232–235.

40. Rosenberg, M. and D. Court. 1979. Regulatory sequences involved in the promotion and termination of RNA transcription. *Ann. Rev. Genet.* 13:319–353.

41. Holmes, M. W., T. Platt, and M. Rosenberg. 1983. Termination of transcription in *E. coli. Cell* 32:1029–1032.

42. Von Hippel, P. H., D. G. Bear, W. D. Morgan, and J. A. McSwiggen. 1984. Protein-nucleic acid interactions in transcription: a molecular analysis. *Ann. Rev. Biochem.* 53:389–446.

43. Cabib, E. 1988. Assay for chitinase using tritiated chitin. *Methods Enzymol.* 161:424–426.

44. Simon, R., U. Priefer, and A. Puhler. 1983. A broad host range mobilization system for in vivo genetic engineering: transposon mutagenesis in gram negative bacteria. *Biotechnology* 1:784–791.

45. Taylor, R. K., C. Manoil, and J. J. Mekalanos. 1989. Broad-host-range vectors for delivery of TnphoA: Use in genetic analysis of secreted virulence determinants of *Vibrio cholerae. J. Bacteriol.* 171:1870–1878.

46. Miller, V. L. and J. J. Mekalanos. 1988. A novel suicide vector and its use in construction of insertion mutations: osmoregulation of outer membrane proteins and virulence determinants in *Vibrio cholerae* requires taxR. *J. Bacteriol.* 170:2575–2583.

47. Milton, D. L., A. Norqvist, and H. Wolf-Watz. 1992. Cloning a metalloprotease gene involved in the virulence mechanism of *Vibrio anguillarum. J. Bacteriol.* 174:7235–7244.

48. Bassler, B. L., C. Yu, Y. C. Lee, and S. Roseman. 1991. Chitin utilization by marine bacteria: degradation and catabolism of chitin oligosaccharides by *Vibrio furnissii. J. Biol. Chem.* 266:24276–24286.

49. Yu, C., A. M. Lee, B. L. Bassler, and S. Roseman. 1991. Chitin utilization by marine bacteria: a physiological function for bacterial adhesion to immobilized carbohydrates. *J. Biol. Chem.* 266:24260–24267.

50. Bassler, B. L., P. J. Gibbons, C. Yu, and S. Roseman. 1991. Chitin utilization by marine bacteria: chemotaxis to chitin oligosaccharides by *Vibrio furnissii. J. Biol. Chem.* 266:24268–24275.

51. John, M., H. Rohrig, J. Schmidt, U. Wieneke, and J. Schell. 1993. Rhizobium NodB protein involved in nodulation signal synthesis is a chitinoligosaccharide deacetylase. *Proc. Natl. Acad. Sci., U. S. A.* 90:625–629.

52. Kendra, D. F. and L. A. Hadwiger. 1984. Characterization of the smallest chitosan oligomer that is maximally antifungal to *Fusarium solni* and elicits pisatin formation in *Pisum sativum. Experimental Mycology* 8:276–281.

53. Ryan, C. A. 1994. Commentary: Oligosaccharide signals: From plant defense to parasite offense. *Proc. Natl. Acad. Sci., U. S. A.* 91:1–2.

54. Horowitz, S. T., S. Roseman, and H. J. Blumenthal. 1957. The preparation of glucosamine oligosaccharides. I. Separation. *J. Am. Chem. Soc.* 79:5046–5049.

55. Roseman, S. and J. Ludowieg. 1954. N-Acetylation of the hexosamines. *J. Am. Chem. Soc.* 76:301–302.

56. Roseman, S. and I. Daffner. 1956. Calorimetric method for the determination of glucosamine and galactosamine. *Anal. Chem.* 28:1743–1746.

57. Comb, D. G. and S. Roseman. 1958. Composition and enzymatic synthesis of N-acetylneuraminic acid (sialic acid). *J. Am. Chem. Soc.* 80:497–498.

58. Roseman, S. and D. G. Comb. 1958. The hexosamine moiety of N-acetylneuraminic acid (sialic acid). *J. Am. Chem. Soc.* 80:3166

59. Comb, D. G. and S. Roseman. 1960. The sialic acids. I. The structure and enzymatic synthesis of N-acetylneuraminic acid. *J. Biol. Chem.* 235:2529–2537.

60. Spivak, C. and S. Roseman. 1959. Preparation of N-acetyl-D-mannosamine and D-mannosamine hydrochloride. *J. Am. Chem. Soc.* 81:2403–2404.

61. Stock, J. B., B. Rauch, and S. Roseman. 1977. Periplasmic space in *Salmonella typhimurium* and *Escherichia coli. J. Biol. Chem.* 252:7850–7861.

62. Imoto, T., L. N. Johnson, A. C. T. North, D. C. Phillips, and J. A. Rupley. 1972. *Vertebrate Lysozymes*. 3rd Edition:666–868. Abstract.

63. Pegg, G. F. 1988. Chitinase from tomato. Methods in Enzymology (Wood and Kellogg, eds.), Vol. 181 Part B, 484–489.

SEQUENCE LISTING:

SEQ ID NO:1 is the nucleotide sequence for the gene encoding periplasmic chitodextrinase.

SEQ ID NO:2 is the amino acid sequence for periplasmic chitodextrinase.

SEQ ID NO:3 is the nucleotide sequence for the gene encoding periplasmic β-GlcNAcidase.

SEQ ID NO:4 is the amino acid sequence for periplasmic β-GlcNAcidase.

SEQ ID NO:5 is the nucleotide sequence for the gene encoding aryl β-N-acetylglucosaminidase.

SEQ ID NO:6 is the amino acid sequence for aryl β-N-acetylglucosaminidase.

---

What is claimed is:

1. An isolated polynucleotide comprising SEQ ID NO:1 and encoding Endo-I polypeptide characterized as:
   a) a periplasmic chitodextrinase;
   b) an endoenzyme;
   c) hydrolyzes soluble chitin oligosaccharides to produce $(GlcNAc)_2$ and/or $(GlcNac)_3$; and
   d) encodes an amino acid sequence as set forth in SEQ ID NO:2.

2. The polynucleotide of claim 1, having a nucleotide sequence as set forth in SEQ ID NO:1.

3. A recombinant expression vector which contains the polynucleotide of claim 1.

4. A host cell which contains the expression vector of claim 3.

5. *Vibrio furnissii* strain SR1545.15.

6. *Vibrio furnissii* strain SR1540.11.

* * * * *